(12) United States Patent
Khan

(10) Patent No.: US 10,653,428 B2
(45) Date of Patent: May 19, 2020

(54) ENDOSCOPIC SNARE COMBINED WITH A CLIP APPLIER

(71) Applicant: Mubashir H. Khan, Springfield, MO (US)

(72) Inventor: Mubashir H. Khan, Springfield, MO (US)

( * ) Notice: Subject to any disclaimer, the term of this patent is extended or adjusted under 35 U.S.C. 154(b) by 265 days.

(21) Appl. No.: 15/883,371

(22) Filed: Jan. 30, 2018

(65) Prior Publication Data

US 2018/0250011 A1   Sep. 6, 2018

Related U.S. Application Data

(63) Continuation of application No. 14/721,312, filed on May 26, 2015, now abandoned, which is a continuation of application No. 14/276,513, filed on May 13, 2014, now abandoned.

(60) Provisional application No. 62/002,691, filed on May 23, 2014, provisional application No. 62/016,717, filed on Jun. 25, 2014, provisional application No.
(Continued)

(51) Int. Cl.
| | |
|---|---|
| *A61B 17/122* | (2006.01) |
| *A61B 17/3205* | (2006.01) |
| *A61B 17/10* | (2006.01) |
| *A61B 17/08* | (2006.01) |
| *A61B 17/128* | (2006.01) |
| *A61B 17/00* | (2006.01) |
| *A61B 90/30* | (2016.01) |

(52) U.S. Cl.
CPC .......... *A61B 17/1227* (2013.01); *A61B 17/08* (2013.01); *A61B 17/10* (2013.01); *A61B 17/1285* (2013.01); *A61B 17/32056* (2013.01); *A61B 90/30* (2016.02); *A61B 2017/0034* (2013.01); *A61B 2017/00358* (2013.01); *A61B 2017/1225* (2013.01)

(58) Field of Classification Search
CPC ....... A61B 17/08; A61B 17/083; A61B 17/10; A61B 17/122; A61B 17/1227; A61B 17/128; A61B 17/1285; A61B 17/32056; A61B 2017/0034; A61B 2017/00358; A61B 2017/1225; A61B 2018/1407; A61B 2018/141; A61B 90/30
See application file for complete search history.

(56) References Cited

U.S. PATENT DOCUMENTS

| | | | |
|---|---|---|---|
| 188,355 A | 3/1877 | Goddu | 411/445 |
| 711,169 A | 10/1902 | LeBlanc | 74/127 |

(Continued)

FOREIGN PATENT DOCUMENTS

GB   1 452 185   5/1974   ............. A61B 17/42

*Primary Examiner* — Ryan J. Severson
(74) *Attorney, Agent, or Firm* — Jonathan A. Bay

(57) ABSTRACT

An elongated endoscopic apparatus has an elongated catheter provided with a snare provision for performing a snaring procedure, a surgery clip, and a clip applier for clipping the wound left by the snaring procedure with the surgery clip. Preferably the elongated catheter is formed with an elongated inner tubular conduit that can accommodate a plurality of surgery clips, each having a C-shape characterized by a pair of elongated jaws mated together at a hinge end, wherein the jaws have tip ends forming the head end for the clip and hinge end forms the tail end for the clip when said plurality of clips are loaded into core of the inner tubular conduit in head to tail procession. The clip applier dispenses the clips a single at a time.

18 Claims, 23 Drawing Sheets

Related U.S. Application Data

61/961,842, filed on Oct. 24, 2013, provisional application No. 61/957,306, filed on Jun. 29, 2013, provisional application No. 61/855,313, filed on May 14, 2013.

(56) References Cited

U.S. PATENT DOCUMENTS

| | | | |
|---|---|---|---|
| 861,188 A | 7/1907 | Jones | 411/446 |
| 1,031,431 A | 7/1912 | Dunn | 411/448 |
| 1,878,053 A | 9/1932 | Winger | 192/44 |
| 2,277,931 A | 3/1942 | Moe | 411/444 |
| 2,487,803 A | 11/1949 | Heimann | 411/517 |
| 2,597,344 A | 5/1952 | Lang | 411/449 |
| 2,631,584 A | 3/1953 | Purificato | 606/68 |
| 3,051,499 A | 8/1962 | Minegishi | 277/481 |
| 3,086,208 A | 4/1963 | Eby | 206/339 |
| 3,098,232 A | 7/1963 | Brown | 606/143 |
| 3,498,175 A | 3/1970 | Goodstein | 411/548 |
| 3,958,576 A | 5/1976 | Komiya | 606/142 |
| 4,246,903 A | 1/1981 | Larkin | 606/143 |
| 4,265,226 A | 5/1981 | Cassimally | 606/221 |
| 4,512,345 A * | 4/1985 | Green | A61B 17/128 |
| | | | 606/143 |
| 4,557,263 A | 12/1985 | Green | 606/143 |
| 4,589,416 A | 5/1986 | Green | 606/220 |
| 4,719,917 A | 1/1988 | Barrows et al. | 606/220 |
| 4,796,627 A | 1/1989 | Tucker | 606/143 |
| 4,905,691 A | 3/1990 | Rydell | 606/47 |
| 5,049,152 A | 9/1991 | Simon et al. | 602/14 |
| 5,122,147 A | 6/1992 | Sewell | 606/110 |
| 5,156,609 A * | 10/1992 | Nakao | A61B 17/0682 |
| | | | 227/179.1 |
| 5,207,692 A | 5/1993 | Kraus | 227/901 |
| 5,242,456 A | 9/1993 | Nash | 606/139 |
| 5,282,808 A | 2/1994 | Kovac et al. | 606/143 |
| 5,304,183 A * | 4/1994 | Gourlay | A61B 17/00234 |
| | | | 227/901 |
| 5,336,227 A | 8/1994 | Nakao | 600/106 |
| 5,354,304 A | 10/1994 | Allen | A61B 17/122 |
| 5,366,459 A | 11/1994 | Yoon | 606/151 |
| 5,433,721 A | 7/1995 | Hooven et al. | 606/143 |
| 5,462,558 A | 10/1995 | Kolesa et al. | 606/139 |
| 5,486,182 A | 1/1996 | Nakao | 600/37 |
| 5,535,759 A | 7/1996 | Wilk | 128/898 |
| 5,547,474 A | 8/1996 | Kloeckl et al. | 606/143 |
| 5,626,585 A | 5/1997 | Mittelstadt et al. | 606/143 |
| 5,746,747 A | 5/1998 | McKeating | 606/110 |
| 5,772,379 A | 6/1998 | Evensen | 411/442 |
| 5,814,052 A | 9/1998 | Nakao | 606/110 |
| 5,846,248 A | 12/1998 | Chu | 606/113 |
| 5,906,620 A | 5/1999 | Nakao | 606/113 |
| 6,010,512 A | 1/2000 | Chu | 606/113 |
| 6,015,415 A | 1/2000 | Avellanet | 606/110 |
| 6,071,233 A | 6/2000 | Ishikawa | 600/104 |
| 6,090,129 A | 7/2000 | Ouchi | 606/113 |
| 6,171,315 B1 | 1/2001 | Chu | 606/113 |
| 6,352,541 B1 | 3/2002 | Kienzle | A61B 17/1285 |
| 6,375,661 B2 | 4/2002 | Chu | 606/113 |
| 6,599,298 B1 | 7/2003 | Forster et al. | 606/139 |
| 6,616,654 B2 | 9/2003 | Mollenauer | 606/110 |
| 6,616,659 B1 | 9/2003 | de la Torre | 128/898 |
| 6,679,892 B2 | 1/2004 | Guido | 606/113 |
| 6,843,794 B2 | 1/2005 | Sixto, Jr. et al. | 606/142 |
| 7,001,399 B2 | 2/2006 | Damarati | 606/143 |
| 7,044,947 B2 | 5/2006 | de la Torre | 128/898 |
| 7,081,121 B2 | 7/2006 | Muramatsu et al. | 606/142 |
| 7,094,245 B2 | 8/2006 | Adams et al. | 606/142 |
| 7,223,271 B2 | 5/2007 | Muramatu et al. | 606/143 |
| 7,285,115 B2 | 10/2007 | Terakura | 606/1 |
| 7,635,374 B2 | 12/2009 | Monassevitch | 600/104 |
| 7,648,514 B1 | 1/2010 | Nakao | 606/142 |
| 7,740,639 B2 | 6/2010 | Hummel | 606/139 |
| 8,070,756 B2 | 12/2011 | Secrest | 600/564 |
| 8,080,021 B2 | 12/2011 | Griego | 606/143 |
| 8,123,795 B1 | 2/2012 | Knodel et al. | 623/1.23 |
| 8,407,875 B2 | 4/2013 | Gray et al. | 29/268 |
| 8,439,245 B2 | 5/2013 | Knodel et al. | 227/175.1 |
| 8,631,992 B1 | 1/2014 | Hausen et al. | 227/179.1 |
| 8,652,146 B2 | 2/2014 | Hewitt | 606/113 |
| 8,679,155 B2 | 3/2014 | Knodel et al. | 606/219 |
| 8,979,836 B2 | 3/2015 | Fischer | 606/41 |
| 9,463,039 B2 | 10/2016 | Kuroda | |
| 2001/0000348 A1 | 4/2001 | Chu | 606/113 |
| 2003/0023237 A1 | 1/2003 | Mollenauer | 606/27 |
| 2003/0065335 A1 | 4/2003 | Guido | 606/144 |
| 2003/0236535 A1 | 12/2003 | Onuki | 606/144 |
| 2004/0044335 A1 | 3/2004 | de la Torre | 606/27 |
| 2004/0225183 A1 | 11/2004 | Michlitsch | A61B 1/00135 |
| 2005/0107807 A1 | 5/2005 | Nakao | A61B 17/122 |
| 2005/0107809 A1 | 5/2005 | Litscher et al. | 606/142 |
| 2005/0209590 A1 | 9/2005 | Terakura | 606/47 |
| 2005/0216036 A1 | 9/2005 | Nakao | A61B 17/068 |
| 2006/0235433 A1 | 10/2006 | Secrest | 606/114 |
| 2006/0253128 A1 | 11/2006 | Sekine | 606/139 |
| 2006/0271072 A1 | 11/2006 | Hummel | 606/142 |
| 2007/0213585 A1 | 9/2007 | Monassevitch | 600/104 |
| 2008/0208217 A1 | 8/2008 | Adams | 606/143 |
| 2008/0255427 A1 | 10/2008 | Satake et al. | 600/204 |
| 2009/0069805 A1 | 3/2009 | Fischer | 606/42 |
| 2009/0131749 A1 | 5/2009 | Ahmed | 600/106 |
| 2010/0292715 A1 | 11/2010 | Nering | A61B 17/064 |
| 2011/0112434 A1 | 5/2011 | Ghabrial | 600/564 |
| 2011/0184429 A1 | 7/2011 | Saldinger | 606/113 |
| 2011/0224492 A1 | 9/2011 | Stern | 600/153 |
| 2011/0313437 A1 | 12/2011 | Yeh | A61B 17/122 |
| 2012/0029526 A1 | 2/2012 | Hewitt | 606/113 |
| 2012/0226287 A1 | 9/2012 | Qadeer | 606/113 |
| 2013/0131688 A1 | 5/2013 | Schwartz | 606/113 |
| 2013/0331854 A1 | 12/2013 | Saldinger | 606/113 |
| 2015/0032119 A1 | 1/2015 | Kuroda | 606/113 |
| 2015/0272588 A1 | 10/2015 | Khan | 606/130 |
| 2015/0374392 A1 | 12/2015 | Khan | 606/113 |
| 2016/0095598 A1 | 4/2016 | Khan | 606/143 |
| 2016/0354070 A1 * | 12/2016 | Motai | A61B 18/1477 |
| 2018/0250011 A1 * | 9/2018 | Khan | A61B 17/1285 |

\* cited by examiner

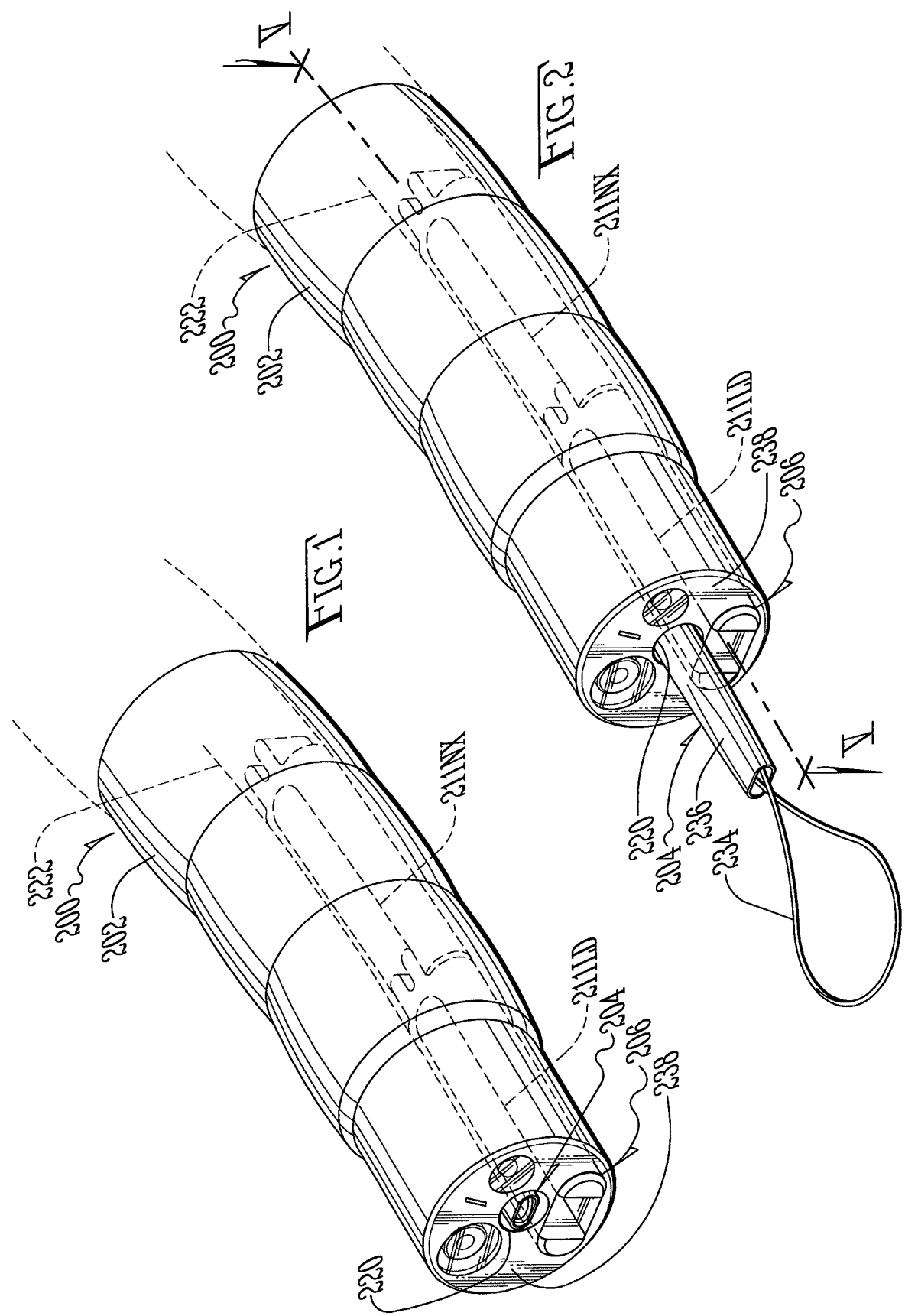

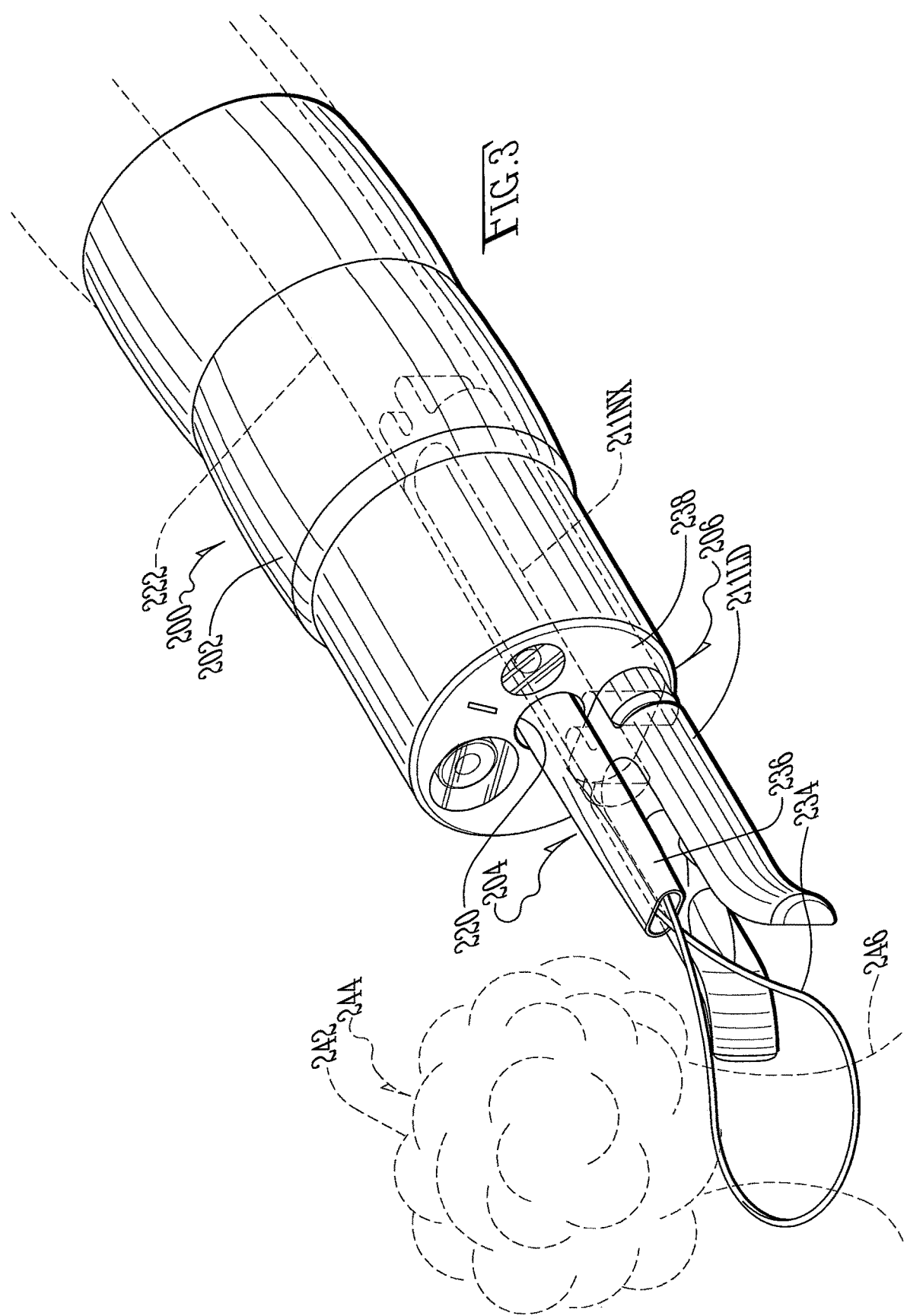

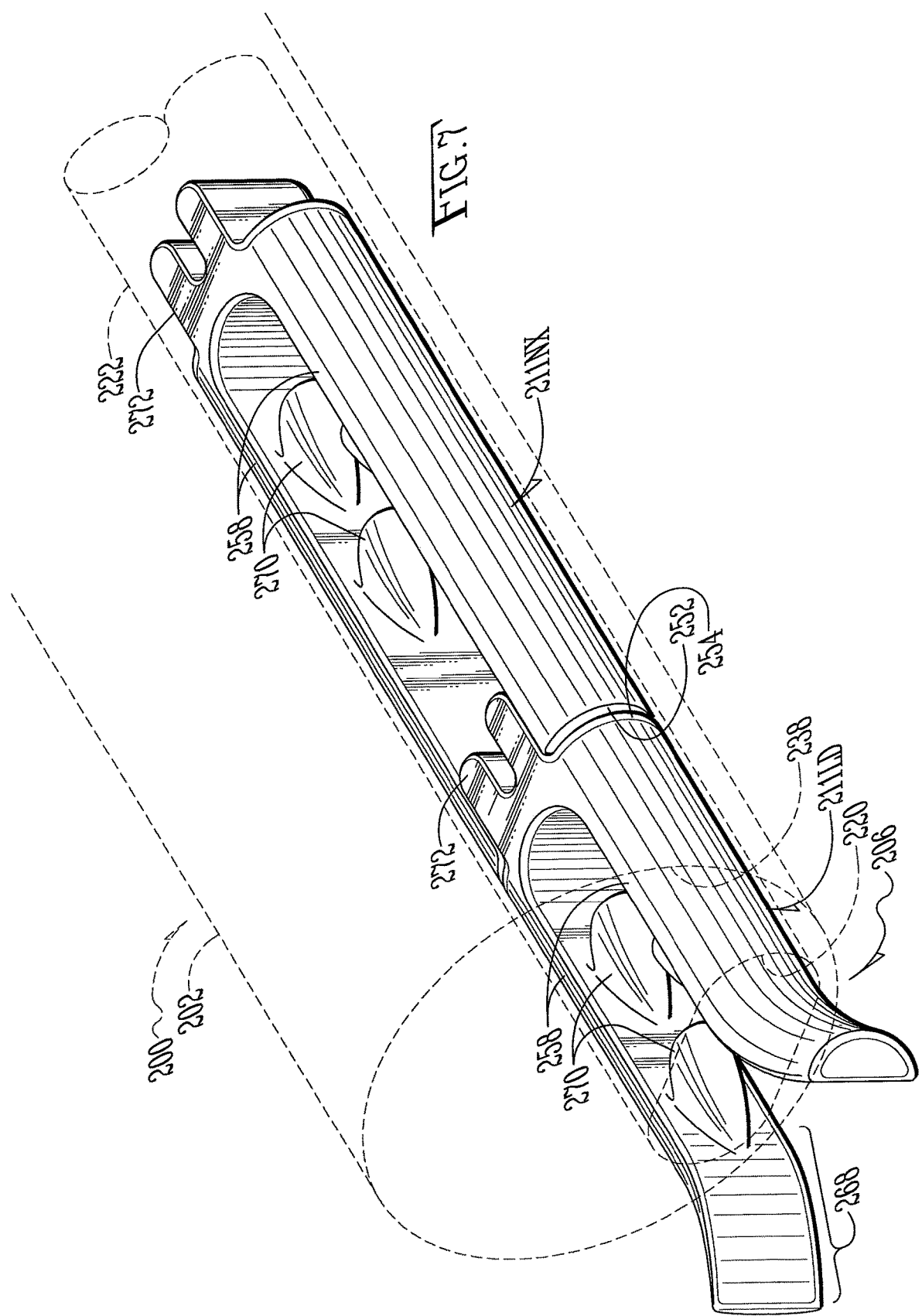

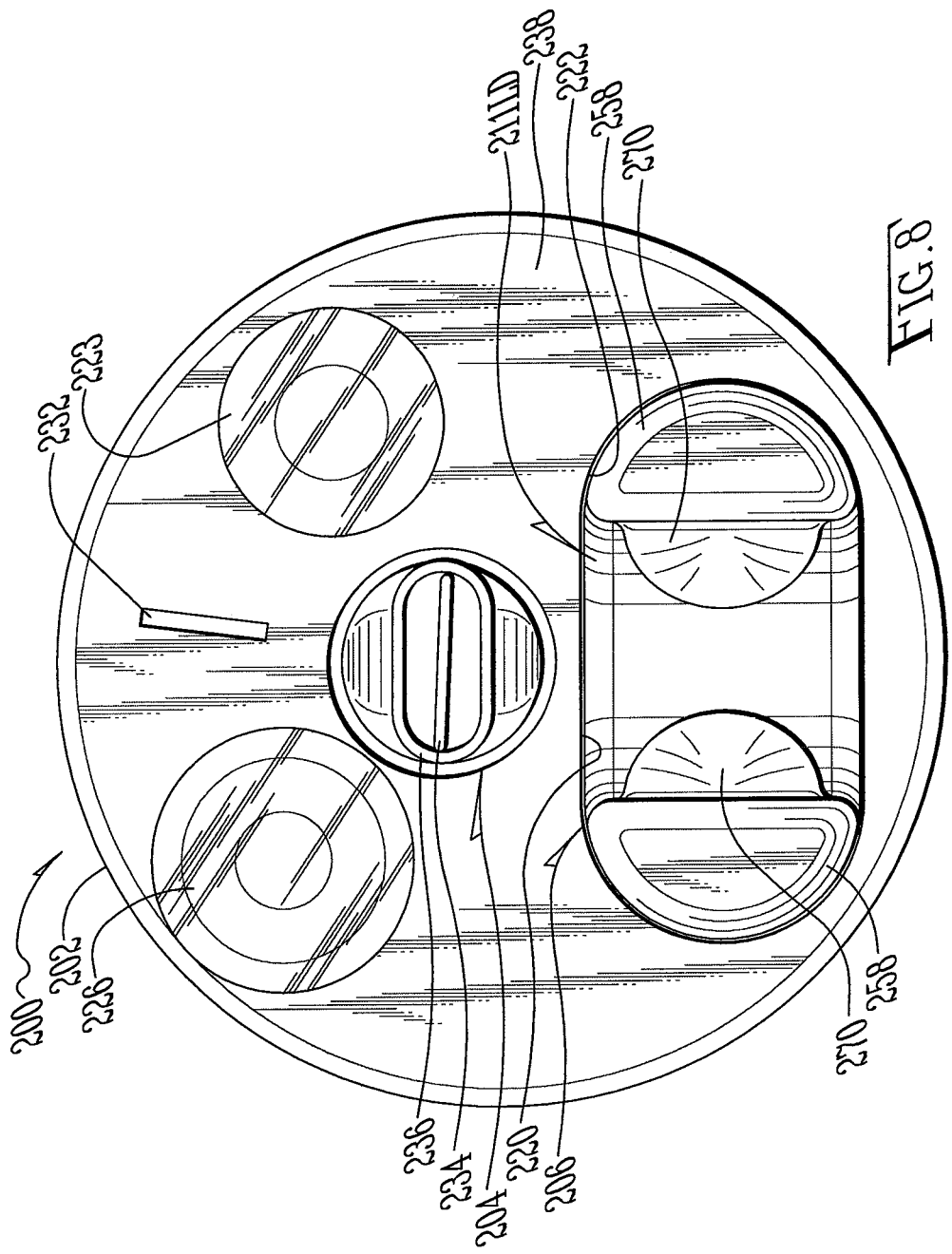

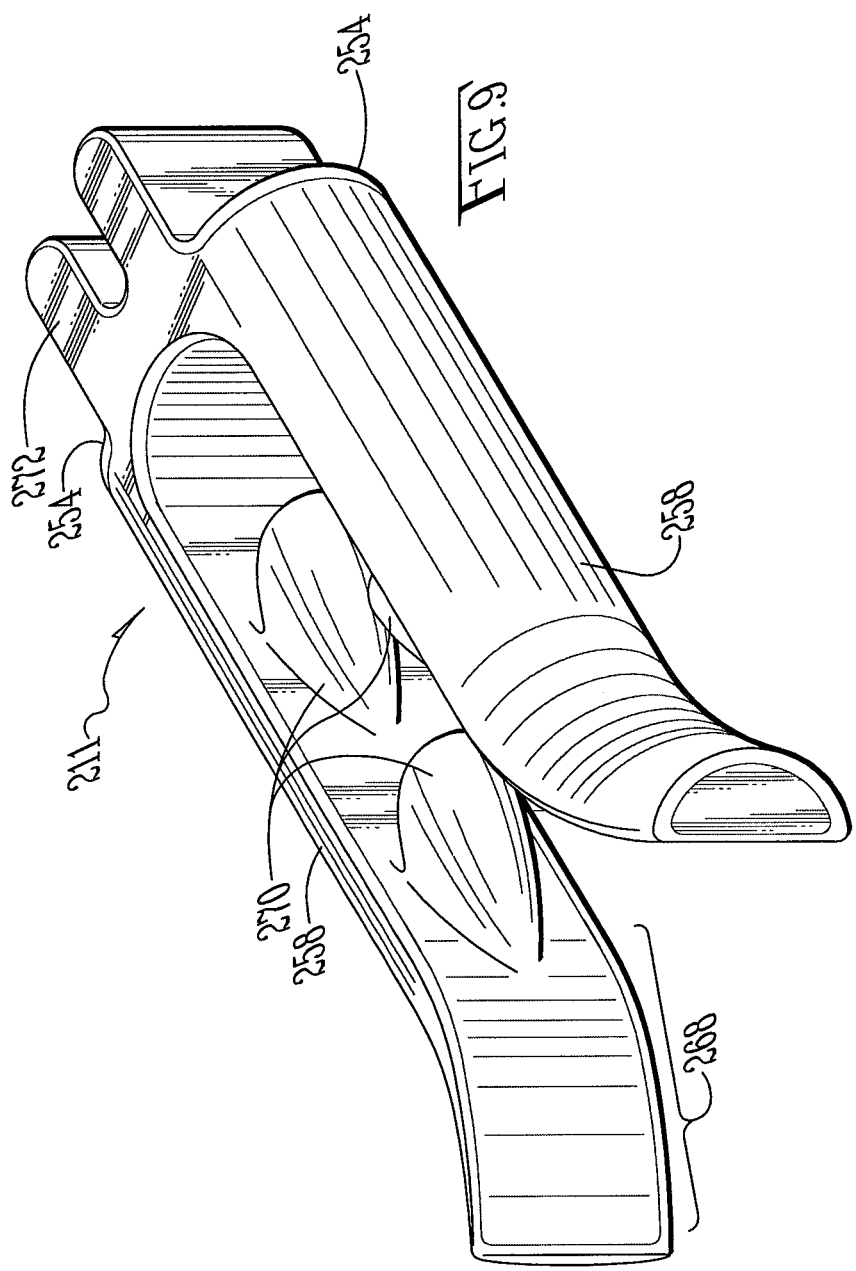

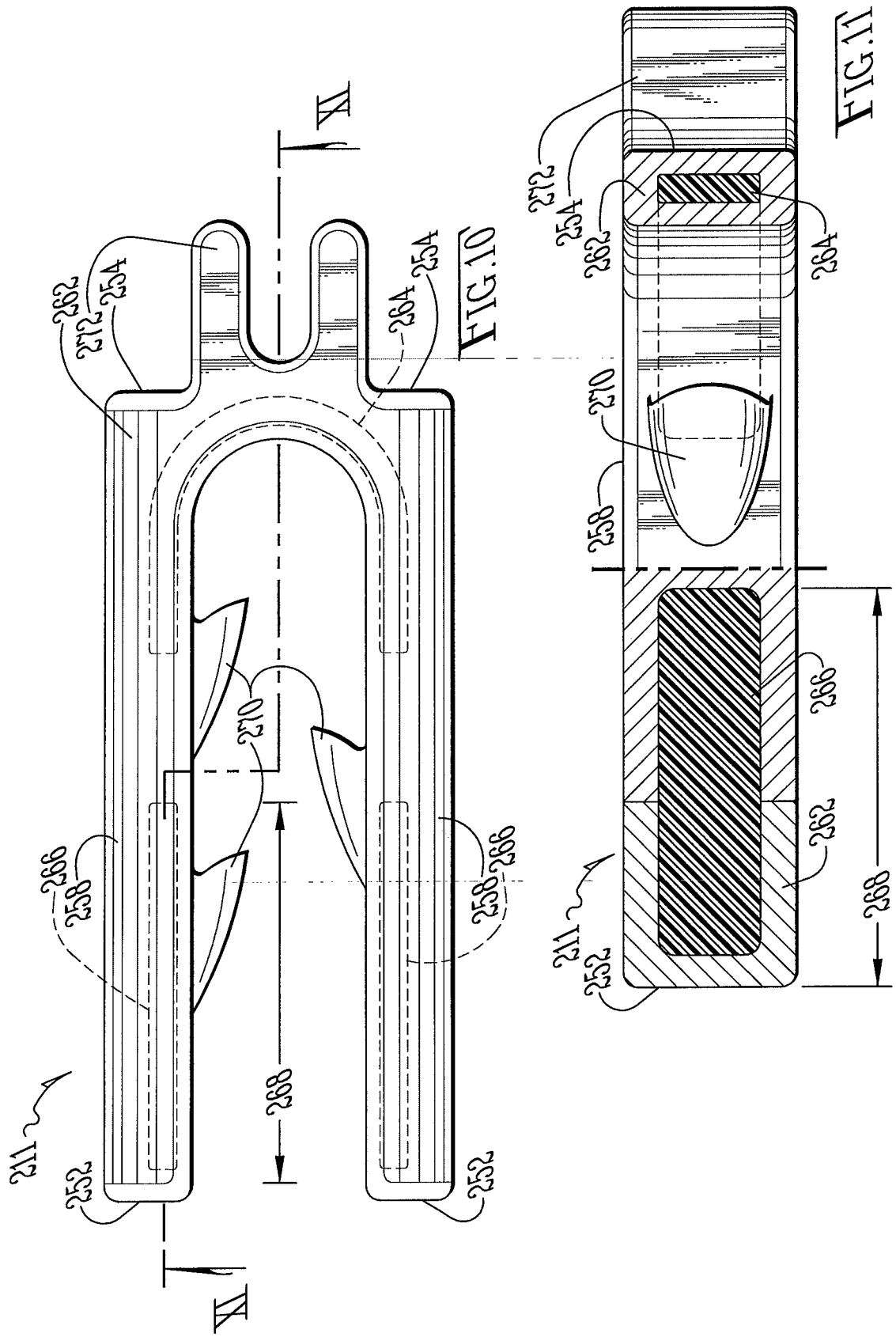

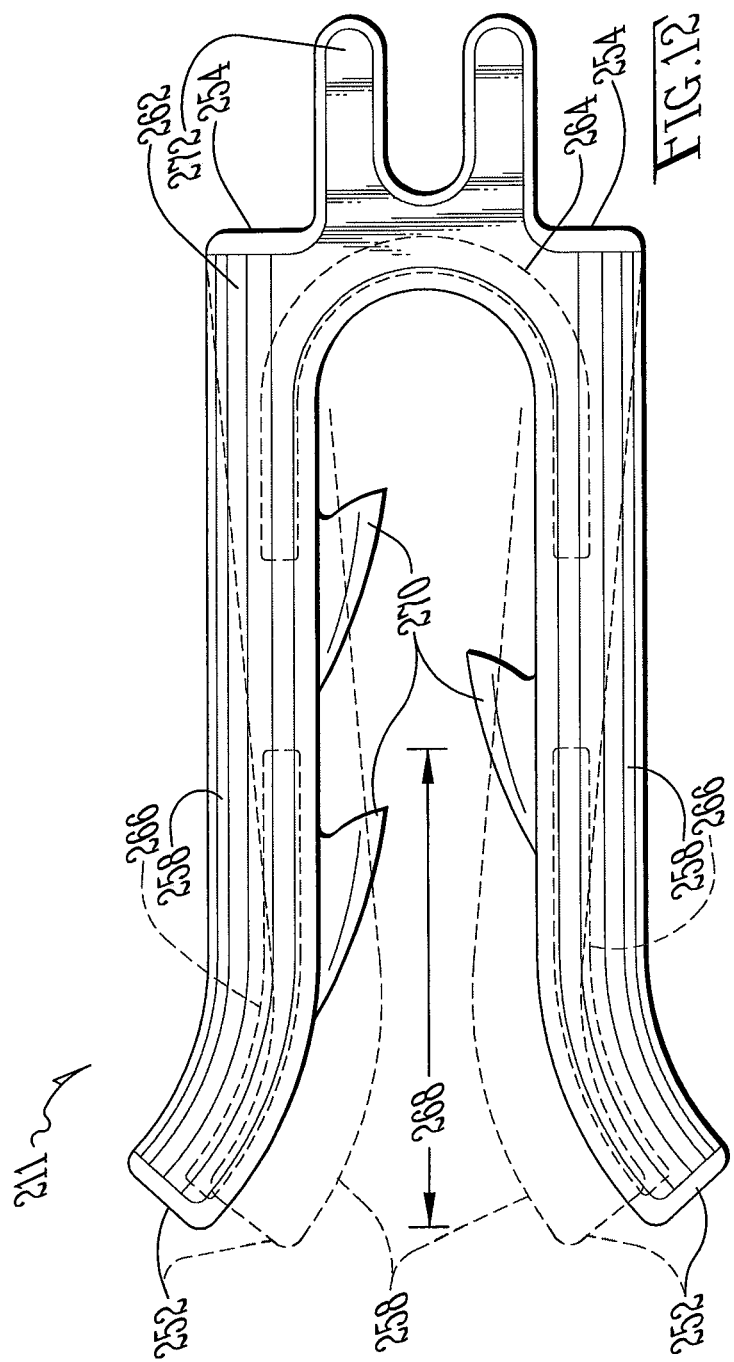

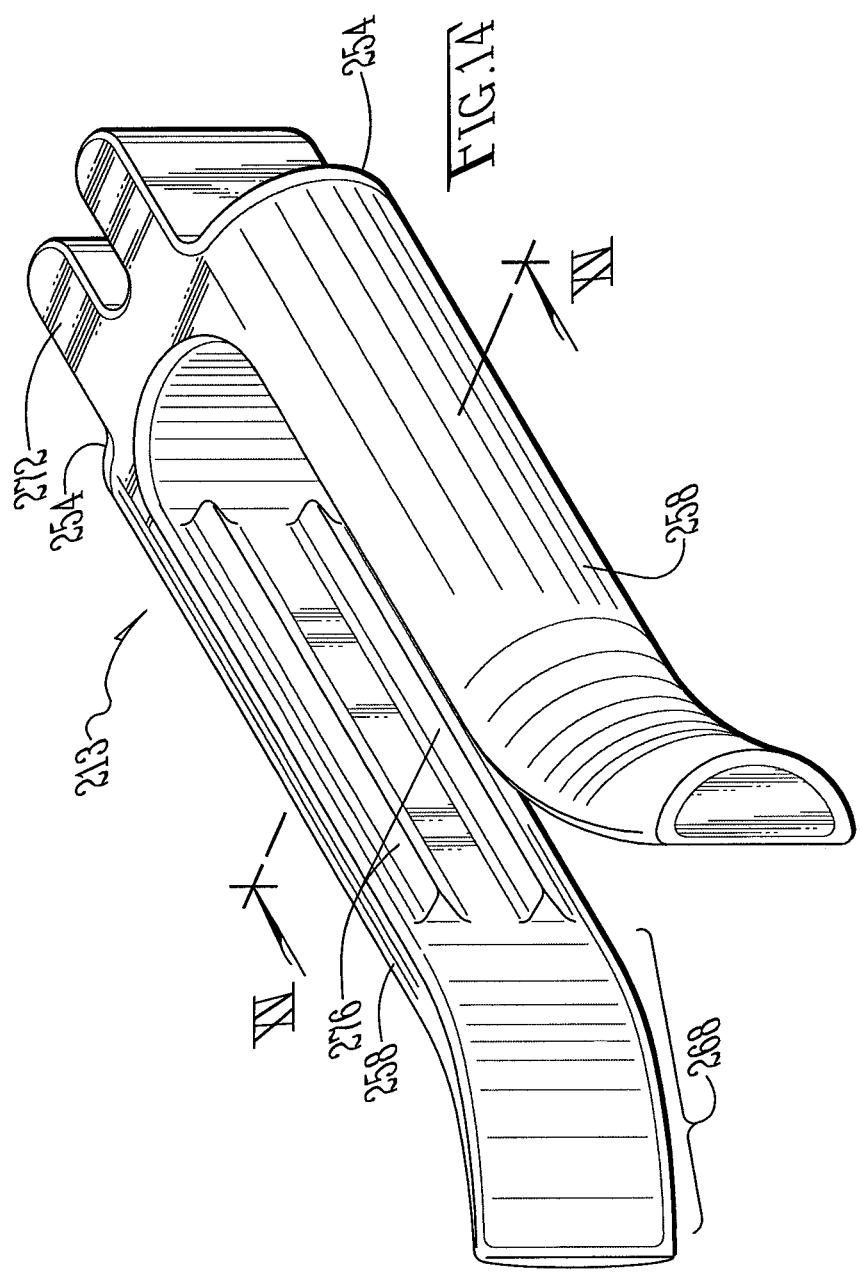

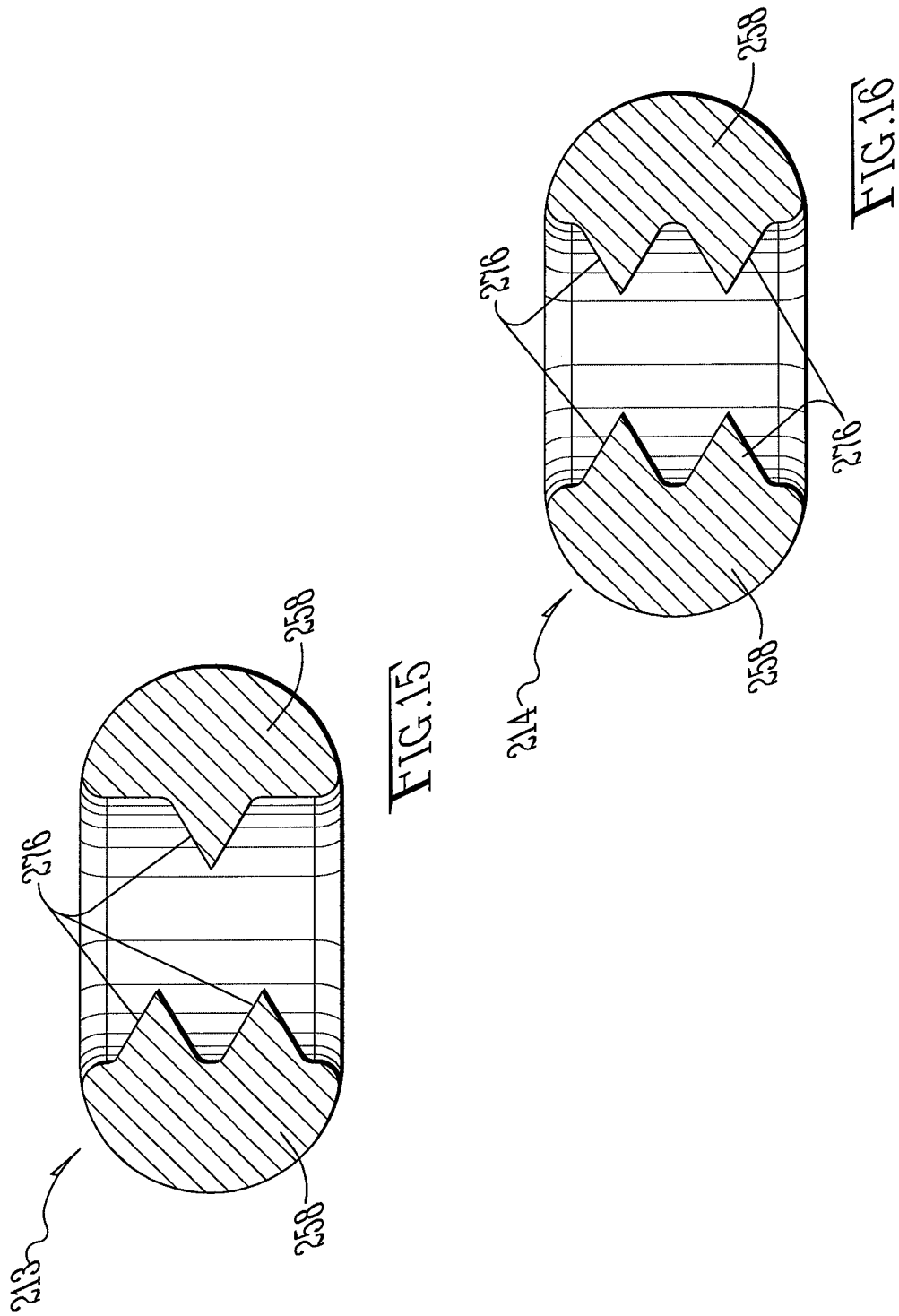

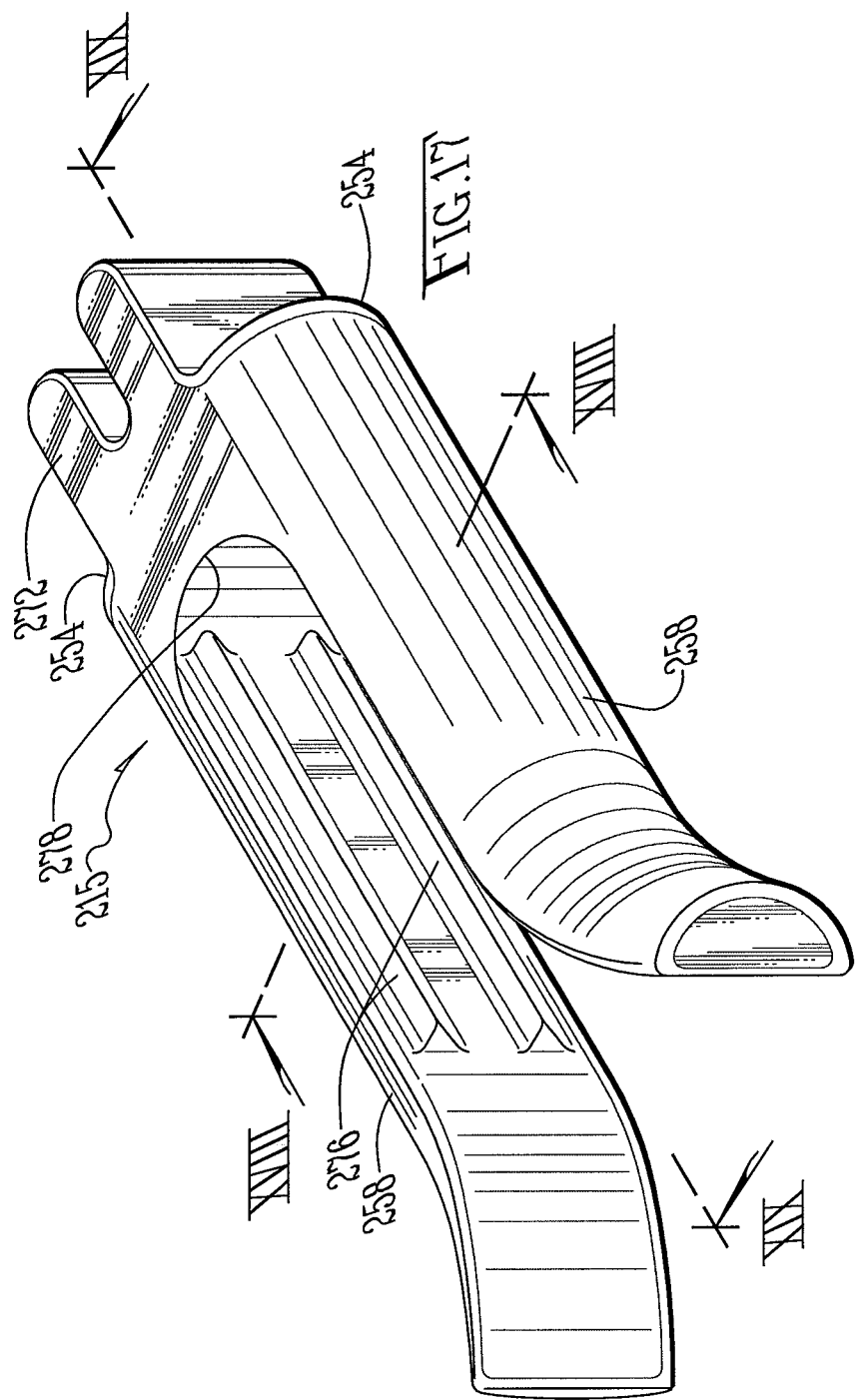

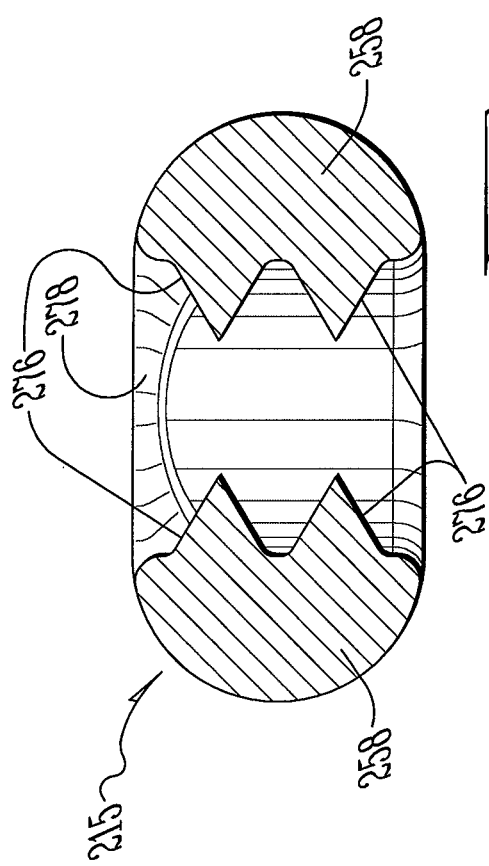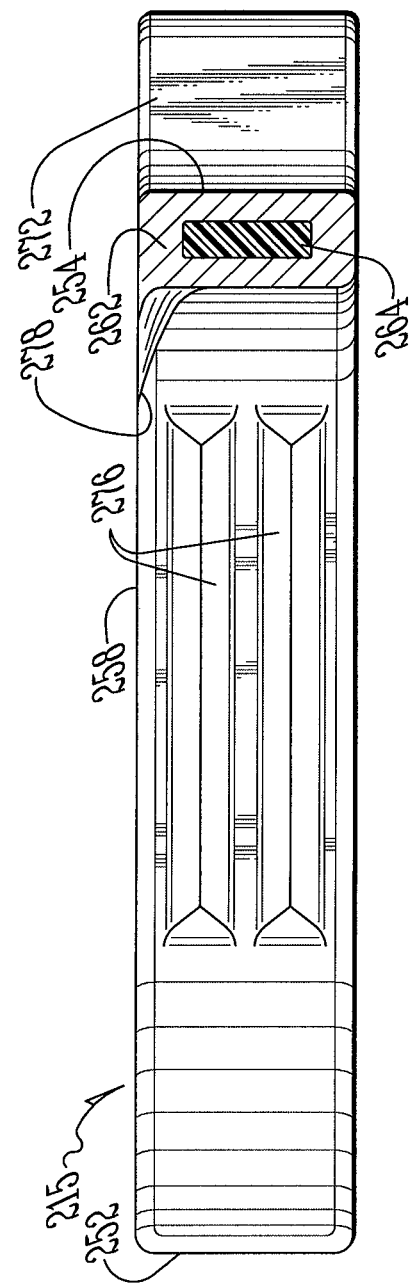

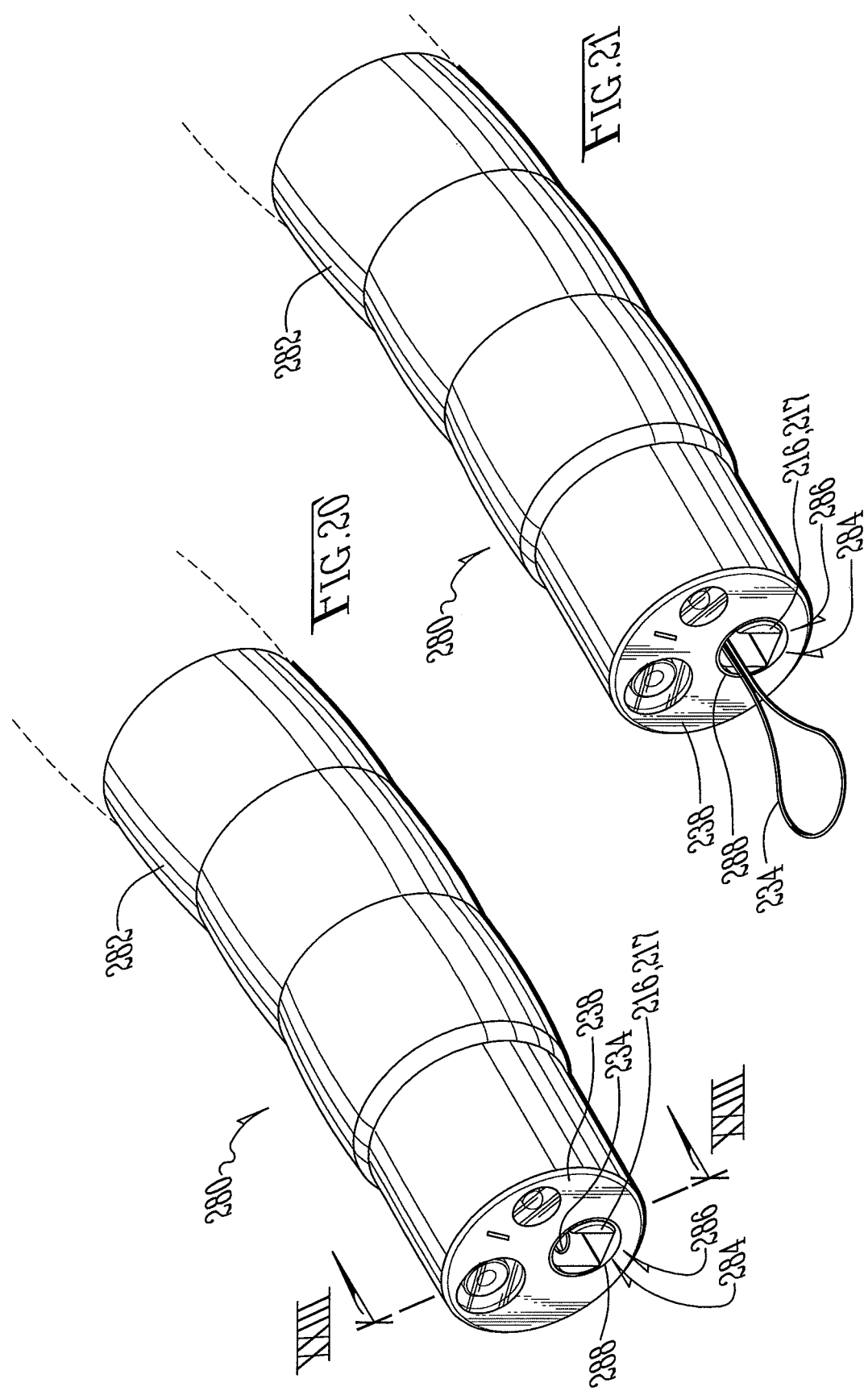

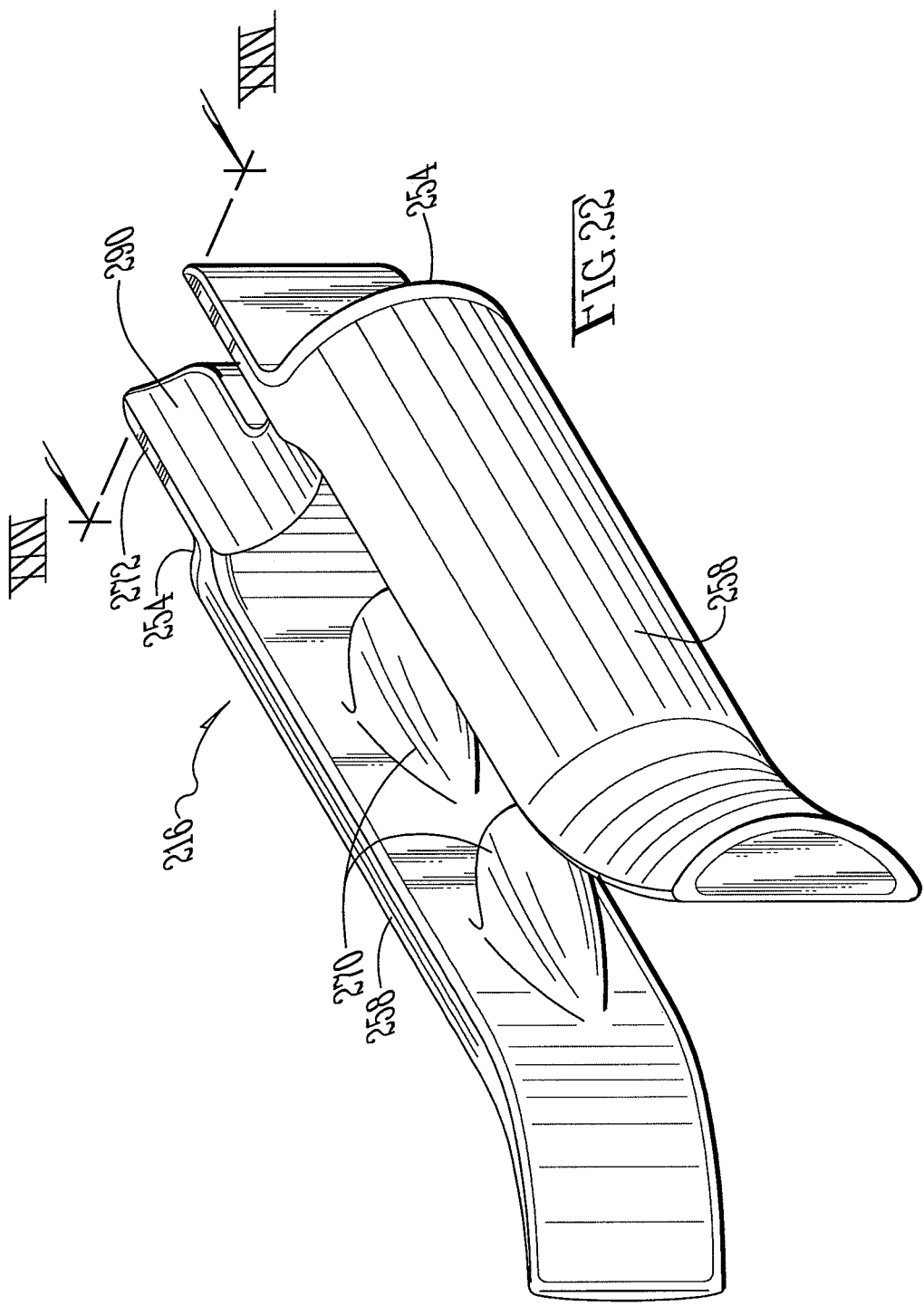

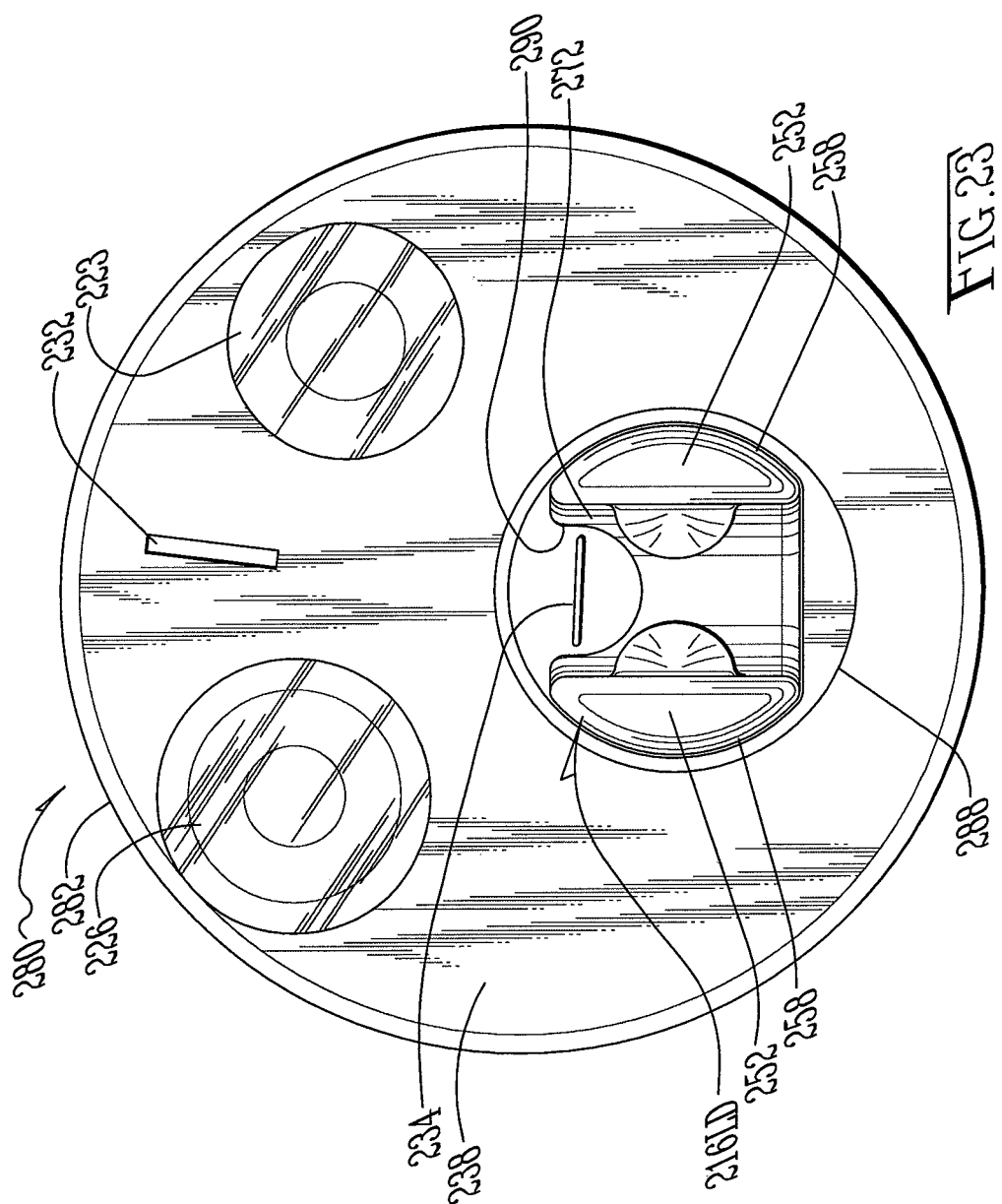

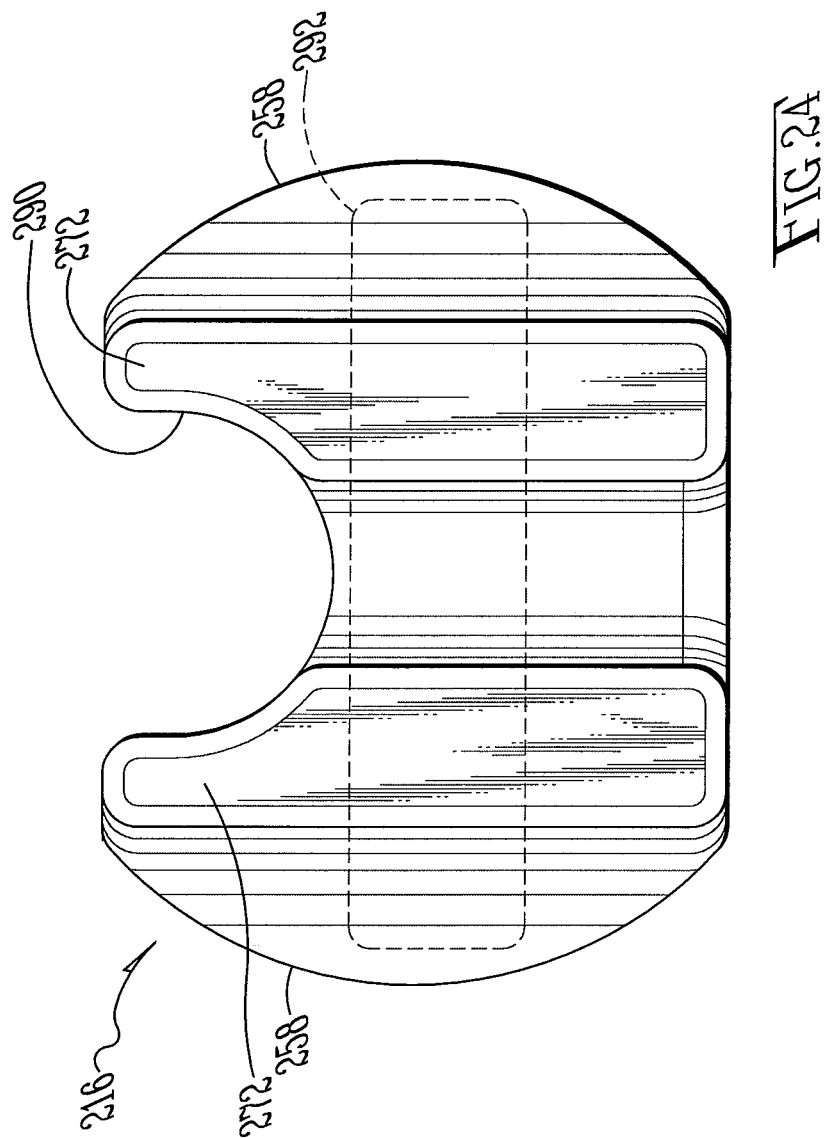

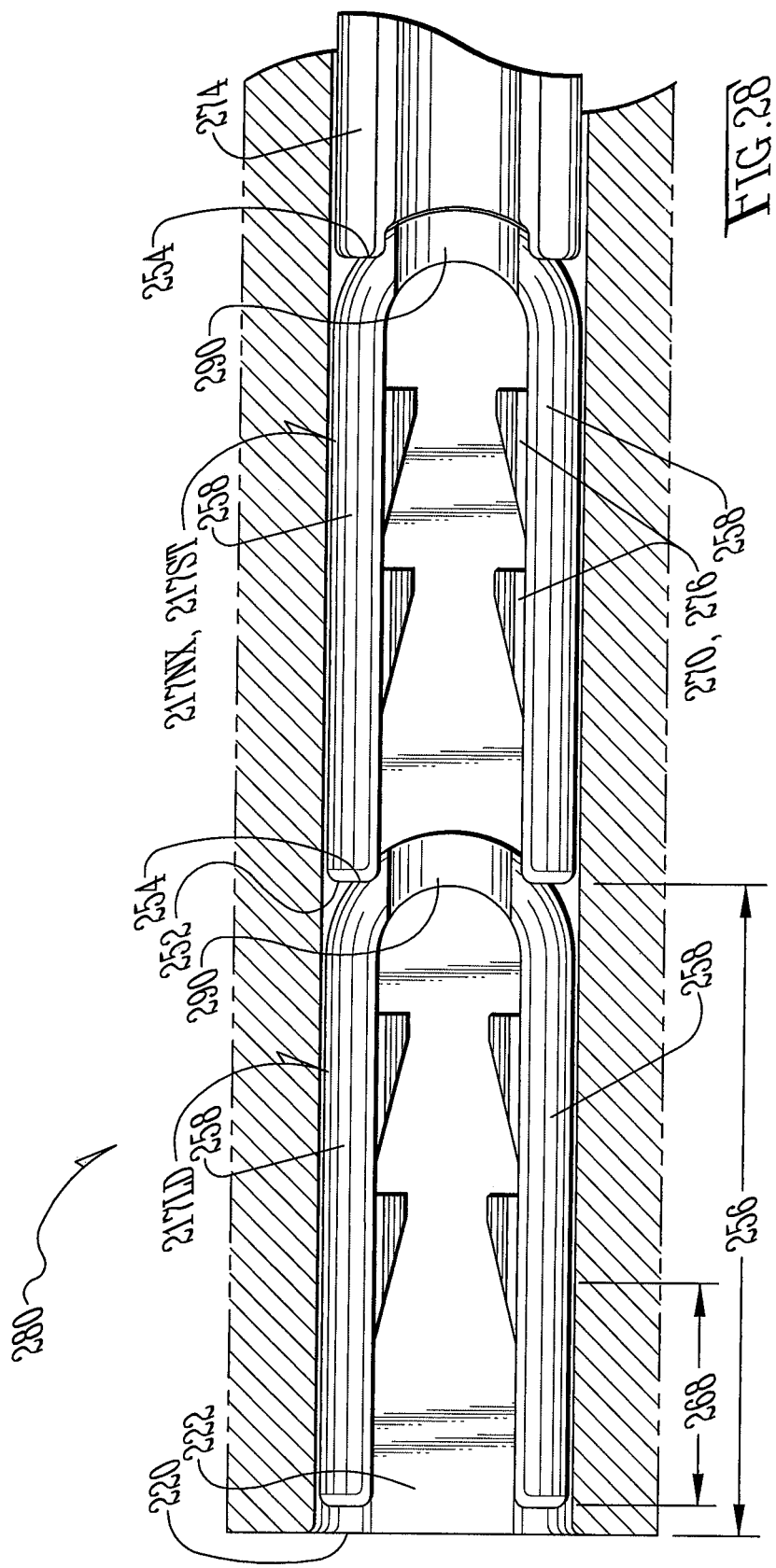

ENDOSCOPIC SNARE COMBINED WITH A CLIP APPLIER

CROSS-REFERENCE TO PROVISIONAL APPLICATION(S)

This application is a continuation of U.S. patent application Ser. No. 14/721,312, filed May 26, 2015, which claims the benefit of U.S. Provisional Application No. 62/002,691, filed May 23, 2014; and U.S. Provisional Application No. 62/016,717, filed Jun. 25, 2014.

U.S. patent application Ser. No. 14/721,312, filed May 26, 2015, is a continuation-in-part of U.S. patent application Ser. No. 14/276,513, filed May 13, 2014, which claims the benefit of U.S. Provisional Application No. 61/961,842, filed Oct. 24, 2013; U.S. Provisional Application No. 61/957,306, accorded filing date of Jun. 29, 2013; and, U.S. Provisional Application No. 61/855,313, accorded filing date of May 14, 2013.

The foregoing disclosures are incorporated herein by this reference thereto.

BACKGROUND AND SUMMARY OF THE INVENTION

The invention relates to surgical instruments and, more particularly, to endoscopic apparatus in which a snare provision for performing polypectomy procedures and the like is combined with a clip applier for clipping the wound left by the snaring operation.

A number of additional features and objects will be apparent in connection with the following discussion of the preferred embodiments and examples with reference to the drawings.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the skills of a person having ordinary skill in the art to which the invention pertains. In the drawings, FIG. 1 is a perspective view of the terminal end of an elongated endoscopic apparatus in accordance with the invention, comprising an elongated catheter in which a snare provision for performing polypectomy procedures (or the like) is combined with a clip applier for clipping the wound left by the snaring procedure by a surgery clip;

FIG. 2 is a perspective view comparable to FIG. 1 except showing the snare provision extended out the terminal end of the endoscopic apparatus;

FIG. 3 is a perspective view comparable to FIG. 2 except showing the extended snare looped over the bulb end of a target piece of anatomy (e.g., a peduncular-style polyp) to sever it off at the stem, and furthermore showing the extension of a surgery clip in accordance with the invention out of a passageway that is hollow axially through the elongated endoscopic apparatus;

FIG. 4 is a perspective view comparable to FIG. 3 except showing the snare tightening around the stem proximate the bulb and showing the jaws of the clips embracing the stem of polyp proximate the anatomical wall it is attached to;

FIG. 7 is a perspective view of the lead clip and second clip of the series of clips in FIG. 6, and in which view the endoscopic apparatus is rendered substantially in hidden lines to show only the general overall outline thereof and the outline of the passageway for the series of clips arranged in the head to tail procession;

FIG. 8 is an enlarged-scale end elevation view of FIG. 1;

FIG. 9 is an enlarged-scale perspective view of one such surgery clip in accordance with the invention, in isolation;

FIG. 10 is a top plan view of FIG. 9, except with the jaws shown straightened;

FIG. 11 is an elevational view, partly in section, taken along offset line XI-XI from FIG. 10;

FIG. 12 is a top plan view comparable to FIG. 10 except by showing in one set of dashed lines that the jaws of the clip naturally want to close after ejection from the dispensing end of the passageway, thereby clamping on the embraced anatomy;

FIG. 14 is a perspective view comparable to FIG. 9 except of a third embodiment of a surgery clip in accordance with the invention;

FIG. 15 is a sectional view taken along line XV-XV in FIG. 14;

FIG. 16 is a sectional view comparable to FIG. 15 except of a fourth embodiment of a surgery clip in accordance with the invention;

FIG. 17 is a perspective view comparable to FIGS. 9 and 13 except of a fifth embodiment of a surgery clip in accordance with the invention;

FIG. 18 is a sectional view taken along line XVIII-XVIII in FIG. 17;

FIG. 19 is an elevational view, partly in section, taken along line XIX-XIX from FIG. 17;

FIG. 20 is a perspective view of the terminal end of an alternate embodiment of an elongated endoscopic apparatus in accordance with the invention, and comprising an elongated catheter in which a snare provision for performing polypectomy procedures (or the like) is combined with a clip applier for clipping the wound left remaining by the snaring procedure by a surgery clip, and as issuing from a common single lumen;

FIG. 21 is a perspective view comparable to FIG. 20 except showing the snare provision extending out of the common single lumen shared by both the snare and the clip applier;

FIG. 22 is a perspective view comparable to FIGS. 9, 13 and 17 except of a sixth embodiment of a surgery clip in accordance with the invention;

FIG. 23 is a an enlarged-scale, end elevational view taken in the direction of arrows XXIII-XXIII in FIG. 20;

FIG. 24 is a an enlarged-scale, end elevational view taken in the direction of arrows XXIV-XXIV in FIG. 22;

FIG. 28 is a section view comparable to FIG. 5 and through the passageway for the clips in the endoscopic apparatus of FIG. 20, and for the clip of FIG. 26, showing that the passageway is loaded with a series of such surgery clips in a line where the head of each clip is pushing into the tail of each preceding clip, until the leadmost clip, which is disposed at an ejection station.

DETAILED DESCRIPTION OF THE PREFERRED EMBODIMENTS

Figure 4:
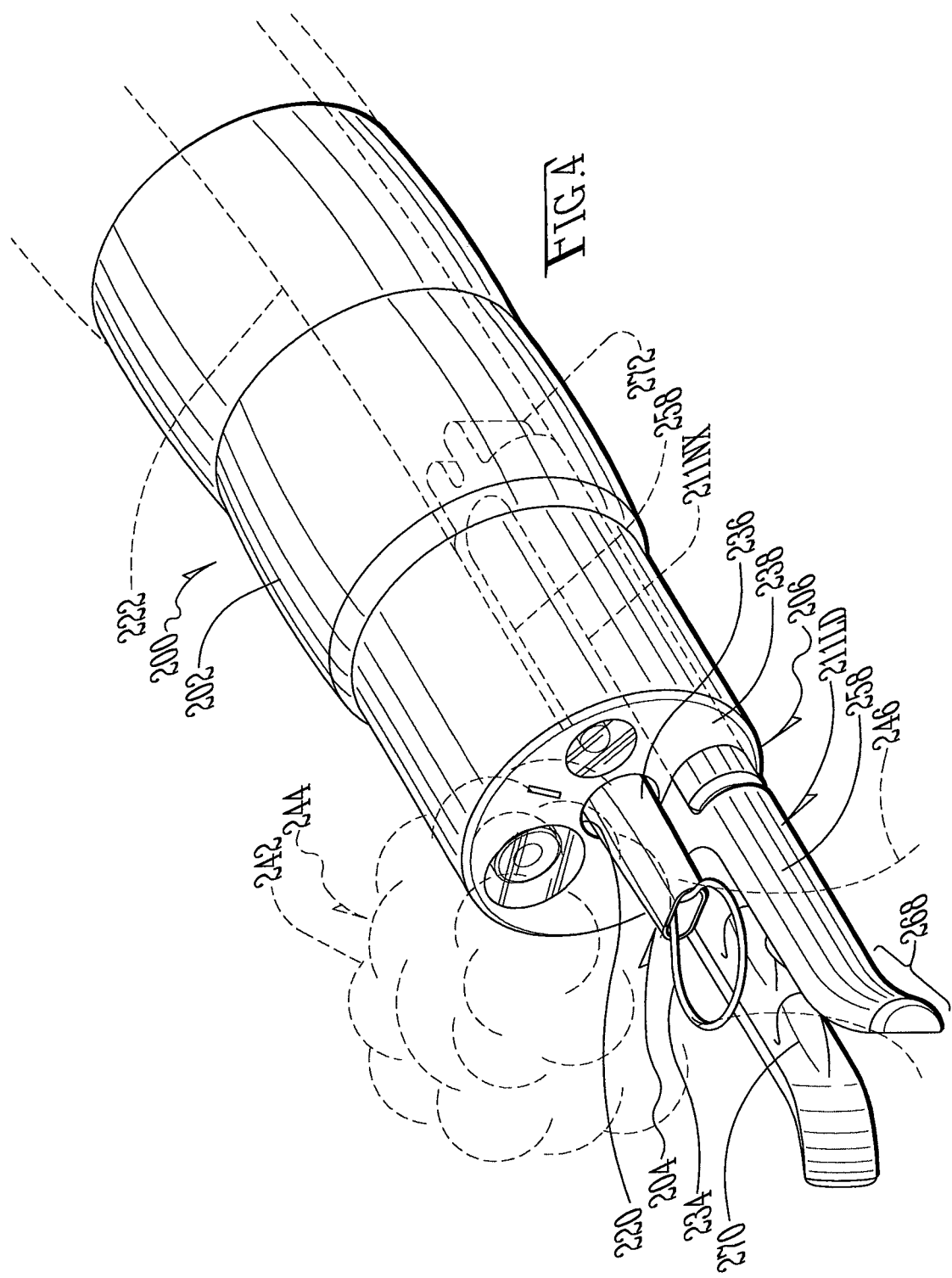

FIGS. 1 through 4 show the terminal end of an elongated endoscopic apparatus 200 in accordance with the invention, comprising a catheter 202 in which a snare provision 204 for performing polypectomy procedures (or the like) is combined with a clip applier 206 for clipping the wound left by the snaring procedure with a clip 211, and more preferably still, a clip 211 in accordance with the invention.

FIG. 8 is an end elevation view on an enlarged scale of the catheter 202 of FIG. 1.

FIG. 8 shows better the following:
the lower ovate opening comprises the dispensing end 220 of the passageway 222 for the procession of surgery clips 211, and the lead clip 211LD is visible too;
the central opening is the access opening 224 for the extension and retraction of the snare provision 204;
the upper left set of concentric circles represents a camera 226;
the upper right pair of concentric circles represents a source 228 of illumination; and
the thin rectangular slot above the snare provision comprises a water nozzle 232 for irrigation purposes.

FIG. 2 shows that the snare provision 204 comprises both the snare 234 proper, which might be a wire noose, and a sleeve 236 therefor. Both the snare 234 and the sleeve 236 are extendible beyond the terminal end 238 of the catheter 202 of the endoscopic apparatus 200. Indeed, it is preferred if the snare 234 and sleeve 236 are independently extendible and retractable. The extension and retraction of the snare 234 and sleeve 236 are controlled by manual controls (not shown) on the opposite end of the catheter 202 of the elongated endoscopic apparatus 200. It is presumed that, the typical person operating the endoscopic apparatus 200 in accordance with the invention is a surgeon.

FIG. 3 shows the extended snare 234 is looped over the bulb end 242 of a target piece of anatomy 244 (eg., a peduncular-style polyp). The object of the procedure is to sever off the bulb 242 at the stem 246, and, apply a clip 211 on the stem 246. FIG. 3 furthermore shows the extension of a surgery clip 211LD in accordance with the invention out of a passageway 222 formed axially through the catheter 202 of the elongated endoscopic apparatus 200.

Figure 5:
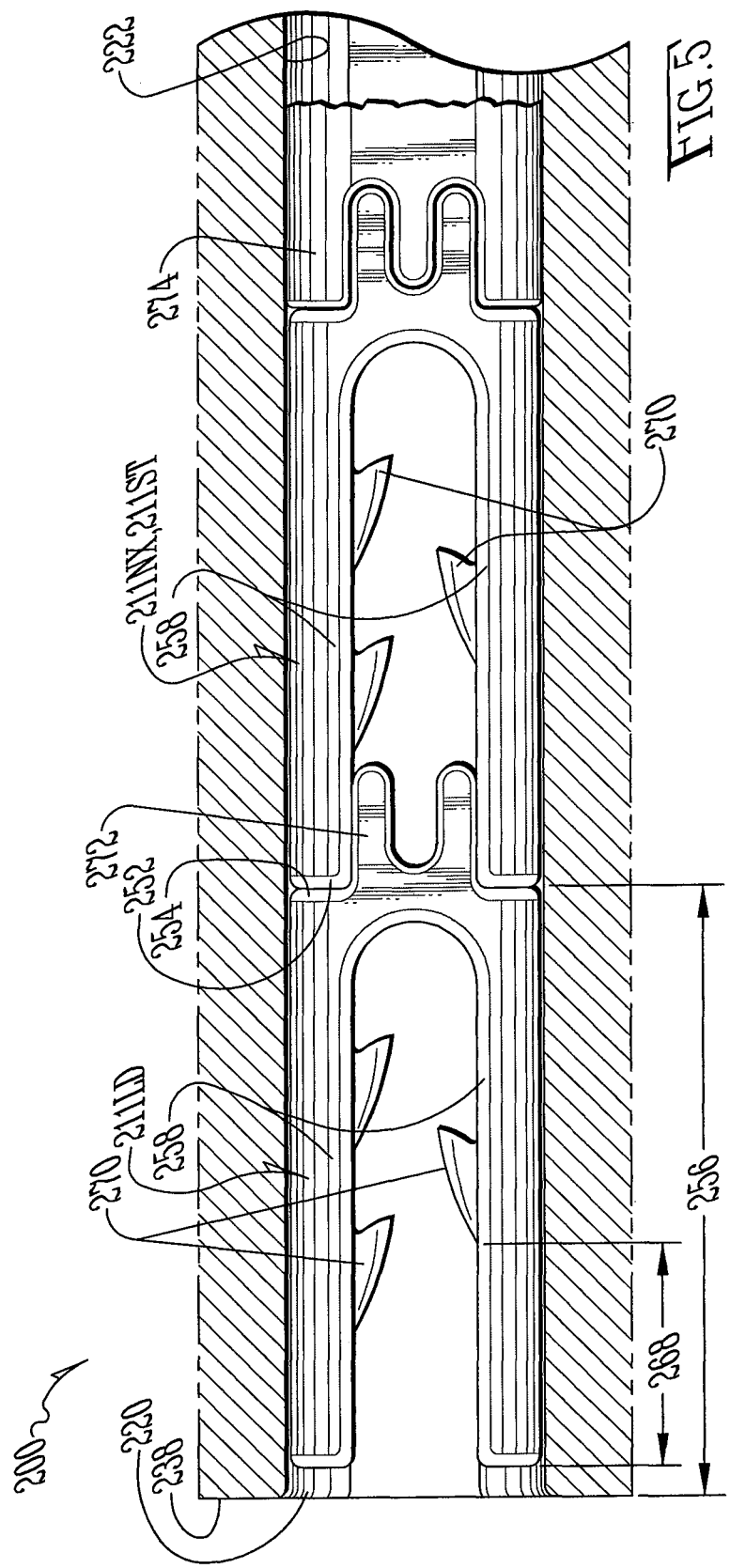
FIG. 5 is a section view of taken along line V-V in FIG. 2 and through the passageway for the clips in the endoscopic apparatus, showing that the passageway is loaded with a series of such surgery clips in a line where the head of each clip is pushing into the tail of each preceding clip, until the leadmost clip, which is disposed at an ejection station.

FIG. 5 is a section view of taken along line V-V in FIG. 2 and through the clip passageway 222 in the catheter 202 of the elongated endoscopic apparatus 200. The clip passageway 222 is loaded with a procession of a plurality of such surgery clips 211 in a series where the head 252 of each clip 211 is pushing into the tail 254 of each preceding clip 211, until the leadmost clip 211LD, which is disposed at an ejection station 256.

FIG. 9 is an enlarged-scale perspective view of one such surgery clip 211 in accordance with the invention, as shown in isolation. FIG. 10 is a top plan view of FIG. 9, except with the jaws 258 shown straightened. FIG. 11 is elevational view, partly in section, taken along offset line XI-XI from FIG. 10.

Returning to FIG. 10, it shows that the clip 211 comprises a composite construction, namely, an encasement 262 resulting in the body and skin of the clip 211 as well as a series of springs 264 and 266 buried inside the encasement 262. Preferably the encasement 262 is constructed of a relatively softer pliant material. For example and without this being any limitation whatsoever other than an illustrative suggestion, the material 262 might comprise a medium density silicone rubber or the like. However, the clip 211 furthermore includes the springs 264 and 266. Preferably, there are three such springs 264 and 266. There is one horseshoe shaped spring 264 at the pivot (or hinge) between the jaws 258 and proximate the tail end 254 of the clip 211. Then there are two other springs 266 buried in the jaws 258 that are proximate the head end 252 of the clip 211.

FIG. 11 shows better that preferably these springs 264 and 266 are constructed not only of a material which is resilient and allows pre-biasing, but also of material which is likely of a higher density.

FIG. 12 is a top plan view comparable to FIG. 10 except showing by one set of dashed lines that the jaws 258 of the clip 211 naturally want to close after ejection from the dispensing end 220 of the passageway 222 (eg., see FIG. 3 or 4), and thereby clamp on the embraced anatomy 246. Preferably this is accomplished by the horseshoe shaped spring 264 at the pivot (or hinge) between the jaws 258 and proximate the tail end 254 of the clip 211.

So in FIG. 12, there is a first set of dashed lines which represent the encased springs 264 and 266, except showing the disposition of the springs 264 and 266 for the clip 211 as drawn in solid lines. The second set of dashed lines shows the relaxed shaped or position for the jaws 258, which is the shape or position that the jaws 258 naturally want to return to after ejection from the passageway 222 (eg., see FIG. 3 or 4). This shape is obtained by shaping the springs 264 and 266 this way for their 'at rest' position.

To return to FIG. 5, it shows a procession of a plurality of clips 211 loaded into the passageway 222 for the clips formed in the elongated endoscopic apparatus 200. The clips 211 do not look like the dashed line rendition in FIG. 12. In fact, the clips 211 are in a flexed position when loaded inside the passageway 222 as shown by FIG. 5. It is only when a clip 211 is ejected that it flares its 'gums' 268 apart at the head end 252 and bites with its 'molars' 270 in the middle, and as shown in dashed lines in FIG. 12.

In FIG. 5, two factors are constraining the clips 211 in that flexed position. Whereas FIG. 5 seems to show the clips 211 in an un-flexed position, the opposite is true. The clips 211 are constrained to adopt that shape.

Briefly, the clips 211 comprise jaws 258 which lead the way in the procession, and behind the jaws 258 the clips 211 then have trailing lever protrusions 272, wherein the jaws 258 and lever protrusions 272 meet at the pivot (or a hinge) therebetween. The lever protrusions 272 of the lead clip 211LD are stuffed into the jaws 258 of the second clip 211NX (ie., the succeeding clip). Thus the natural bias of the horseshoe-shaped spring 264 cannot force the 'molars' 270 of the second clip 211NX to close. Also, the passageway 222 is very close fitting around the procession of the clips 211. Thus also, the natural bias of the two springs 266 that want to flare open the 'gums' 268 of the clips 211 are constrained as well.

Figure 6:
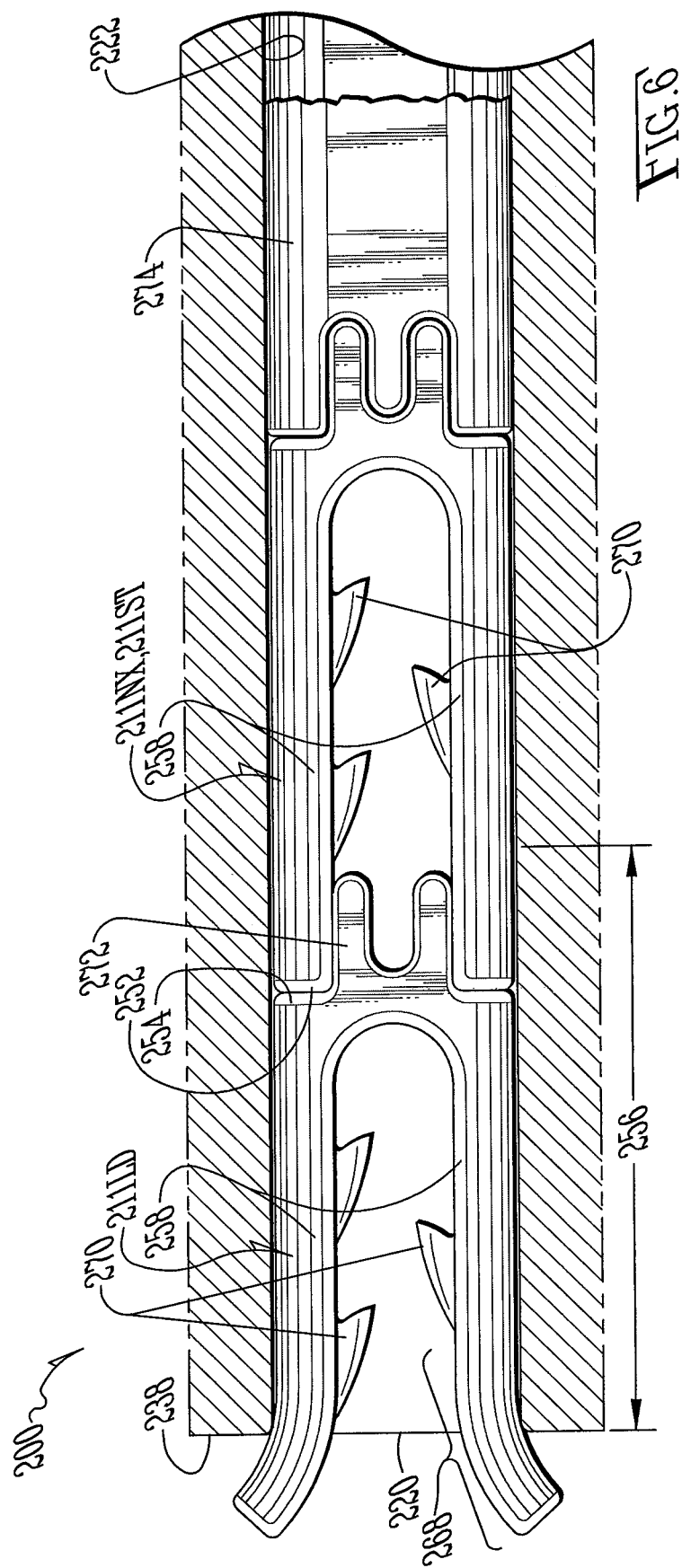
FIG. 6 is a section view comparable to FIG. 5 except showing the lead clip in the beginning stages of being dispensed out the dispensing end of clip passageway.

At last, attention can be returned to FIG. 4. It is a perspective view comparable to FIG. 3 except showing the snare 234 tightening around the stem portion 246 of the target anatomy 244 (eg., polyp) proximate the bulb 242, and also showing the jaws 258 of the clips 211 embracing the stem 246 of polyp 244 proximate the anatomical wall it is attached to. As FIG. 6 shows better, as soon as the jaws 258 of the lead clip 211LD clear the dispensing end 220 of the passageway 222, the 'gums' 268 of the clip 211LD flare. However, the lever protrusions 272 of the lead clip 211LD are still forced inside the jaws 258 of the second clip 211NX (ie., the succeeding clip). Therefore, the action of the horseshoe-shaped spring 264 wanting to cause the 'molars' 270 of the clip 211LD to bite is overcome.

FIG. 4 shows allows imagination of the progression of events in dispensing the lead clip 211LD. The lead clip 211LD starts to poke out of the dispensing end 220 of the passageway 222 and initially the 'gums' 268 flare. That is, the jaws 258 of the lead clip 211LD open wider than how constrained in the passageway 222. This allows the operator (eg., surgeon) to embrace the target anatomy 244/246 between the wide open jaws 258.

While so embraced, the operator (eg., surgeon) then executes the closing of the noose of the snare 234, thereby severing off the bulb 242. If the operator can withdraw the terminal end 238 from the lead clip 211LD, and leave it there in place, then the lead clip 211LD might stay in place. As soon as the trailing lever protrusions 272 of the lead clip 211LD slip out of the jaws 258 of the second clip 211NX, then the 'molars' 270 of the lead clip 211LD 'bite,' ie., apply a clamping pressure on the stem 246 of the polyp 244.

The dispensing end 220 of the clip passageway 222 of the endoscopic apparatus 200 in accordance with the invention could be provided with the following. That is, the dispensing end 220 could be provided with a mechanism for positively launching the lead clip 211LD (ie., separating it from the second clip 211NX or, if the last clip 211ST of procession, the urging/ejecting plunger 274 on the last clip 211ST, and see FIGS. 5 and 6 for such a plunger 274).

FIGS. 5 and 6 also better show that, the jaws 258 are provided with 'molar' teeth 270 which do the work of retaining the clip 211 on the clamped stem 246.

Figure 13:
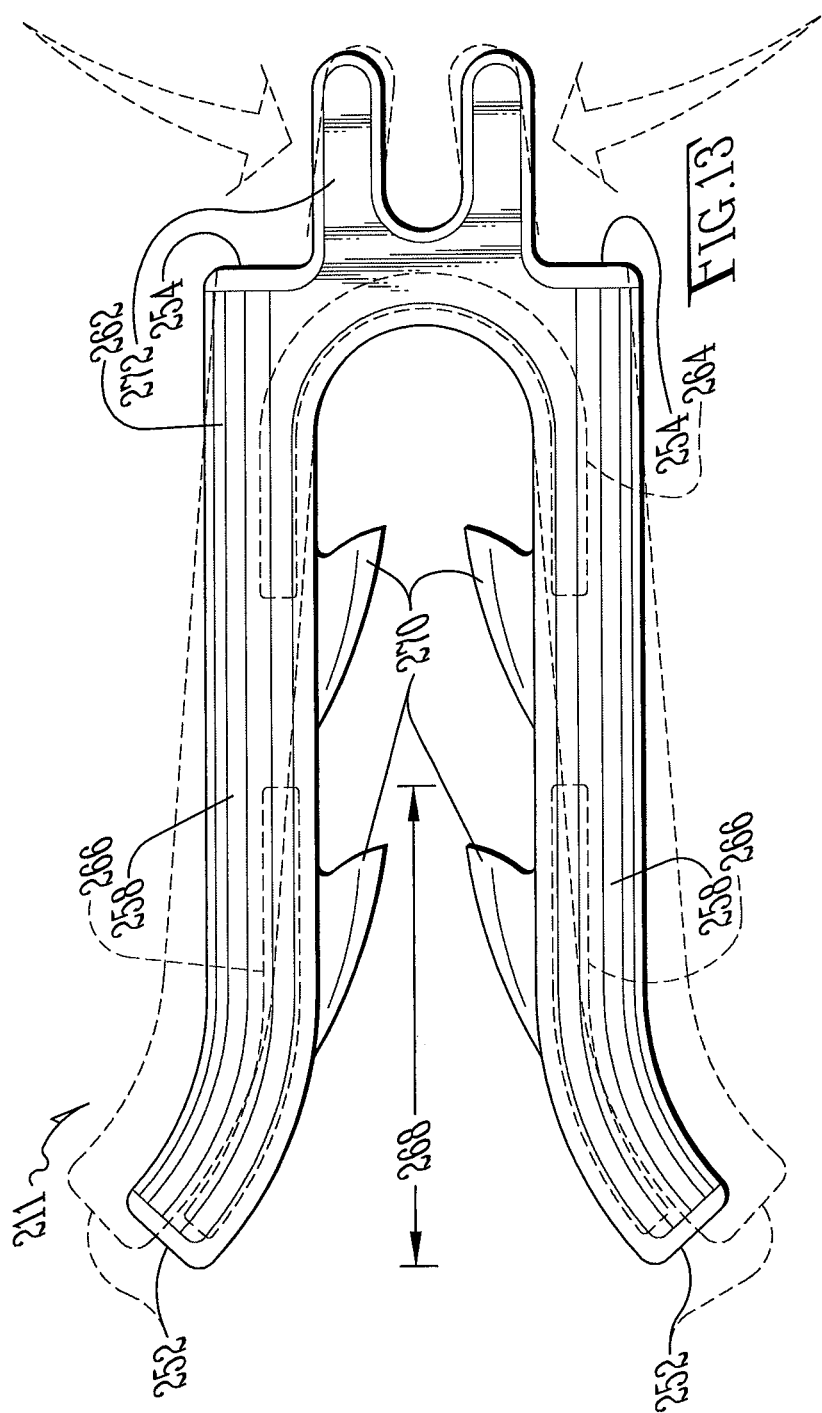
FIG. 13 is a top plan view comparable to FIG. 12 except showing a second embodiment of the clip and also showing in dashed line that the jaws of the clip can be spread apart by an applied pinching force on the trailing lever protrusions of the clip.

FIG. 13 is a top plan view comparable to FIG. 12 except showing a second embodiment of the clip 212. That is, this clip 212 has two 'molars' 270 on each jaw 258. FIG. 12 also shows, in dashed line, that the jaws 258 of the clip 212 can be spread apart by an applied pinching force on the trailing lever protrusions 272 of the clip 212. For example, if the operator (eg., surgeon) did not like the placement of the lead clip 212, the clip 212 can be released by a miniature plier-like tool, and the operator (eg., surgeon) can re-do a second clip 212 in place of the first.

FIGS. 14 and 15 show a third embodiment of a surgery clip 213 in accordance with the invention. These clips do not have 'molars' shaped as barbs as shown previously. Instead, the 'molars' are formed as sets of axial ridges 276.

FIGS. 14 and 15 also show that, preferably the axial ridges 276 are intermeshing. FIG. 16 shows a fourth embodiment of a surgery clip 214 in accordance with the invention, which again has axial ridges 276, but which however are opposing and not intermeshing.

FIGS. 17 through 19 show a fifth embodiment of a surgery clip 215 in accordance with the invention. The chief distinction is best shown in FIG. 19. That is, FIG. 19 is an elevational view, partly in section, taken along line XIX-XIX from FIG. 17.

In all the clips 211 through 215, the jaws meet at a U-shaped bight which forms the pivot (or hinge) for the jaws 258. In FIGS. 17-19, this U-shaped bight is a little different. In FIG. 19, the upper surface of the clip 215 is the surface proximate the snare 234 (not shown in FIGS. 17 through 19, but see FIG. 3). The U-shaped bight proximate the upper surface is formed with a razor edge 278.

That way, the following sequence of events can take place. The snare 234 is looped over the bulb 242 of the polyp 244, and then brought to encircle the stem 246 proximate the bulb 242. The lead clip 215 can be extended and positioned to have its flaring jaws 258 embrace the stem 246. After that, the snare 234 can be tightened in an ever closing noose at the same time that the tightening snare 234 tugs the stem 246 against the razor edge 278 at the back of the U-shaped bight of the clip 215.

In other words, there are two things working together to do the one job of severing the bulb 242 (or whatever other target anatomy). The tightening encirclement of the snare 234, also pulling the stem 246 against the razor edge 278 at the back of the U-shaped bight of the clip 215.

FIGS. 20 through 28 show an alternate embodiment of an elongated endoscopic apparatus 280 in accordance with the invention, and comprising a catheter 282 in which a snare provision 284 for performing polypectomy procedures (or the like) is combined with a clip applier 286 for clipping the wound left remaining by the snaring procedure with a clip 216 or 217, and more preferably still, a clip 216 or 217 in accordance with the invention.

In these views, the snare provision 284 and the dispensing of clips 216/217 is accomplished as both issuing from a common single lumen 288 in the catheter 282 of the elongated endoscopic apparatus 280 in accordance with the invention.

FIGS. 22 and 24-27 show how the clips 216/217 are modified for this implementation by having a recessed groove 290 in them for the snare 234 (or a sleeve for the snare, not shown but see FIG. 2) to occupy therein. The snare 234 and/or sleeve might travel axially in this procession of recessed grooves 290 formed by the procession of clips 216 or 217. Indeed, the snare 234 and/or sleeve might reciprocate axially therein.

Figure 25:
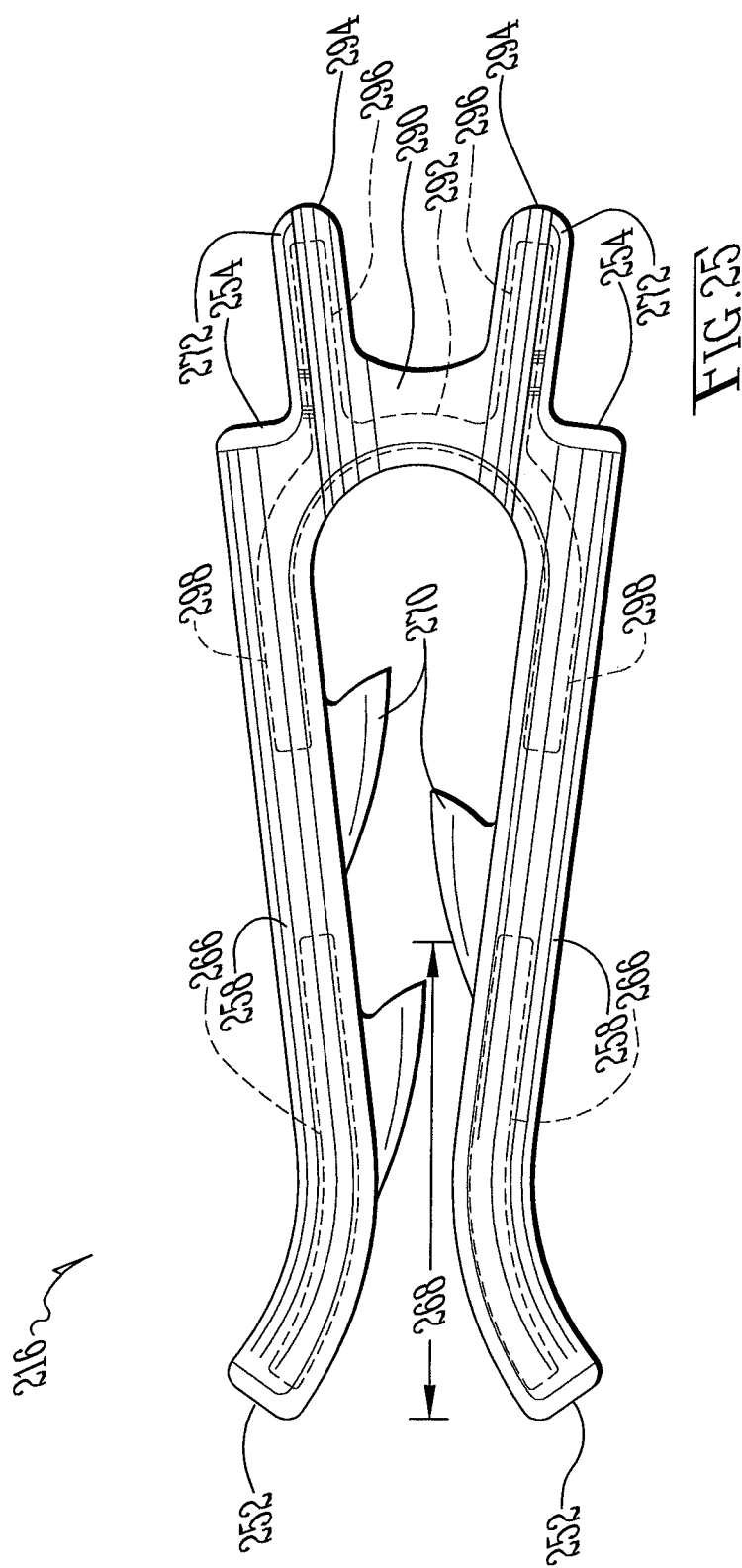
FIG. 25 is a top plan view of FIG. 22.
Figure 26:
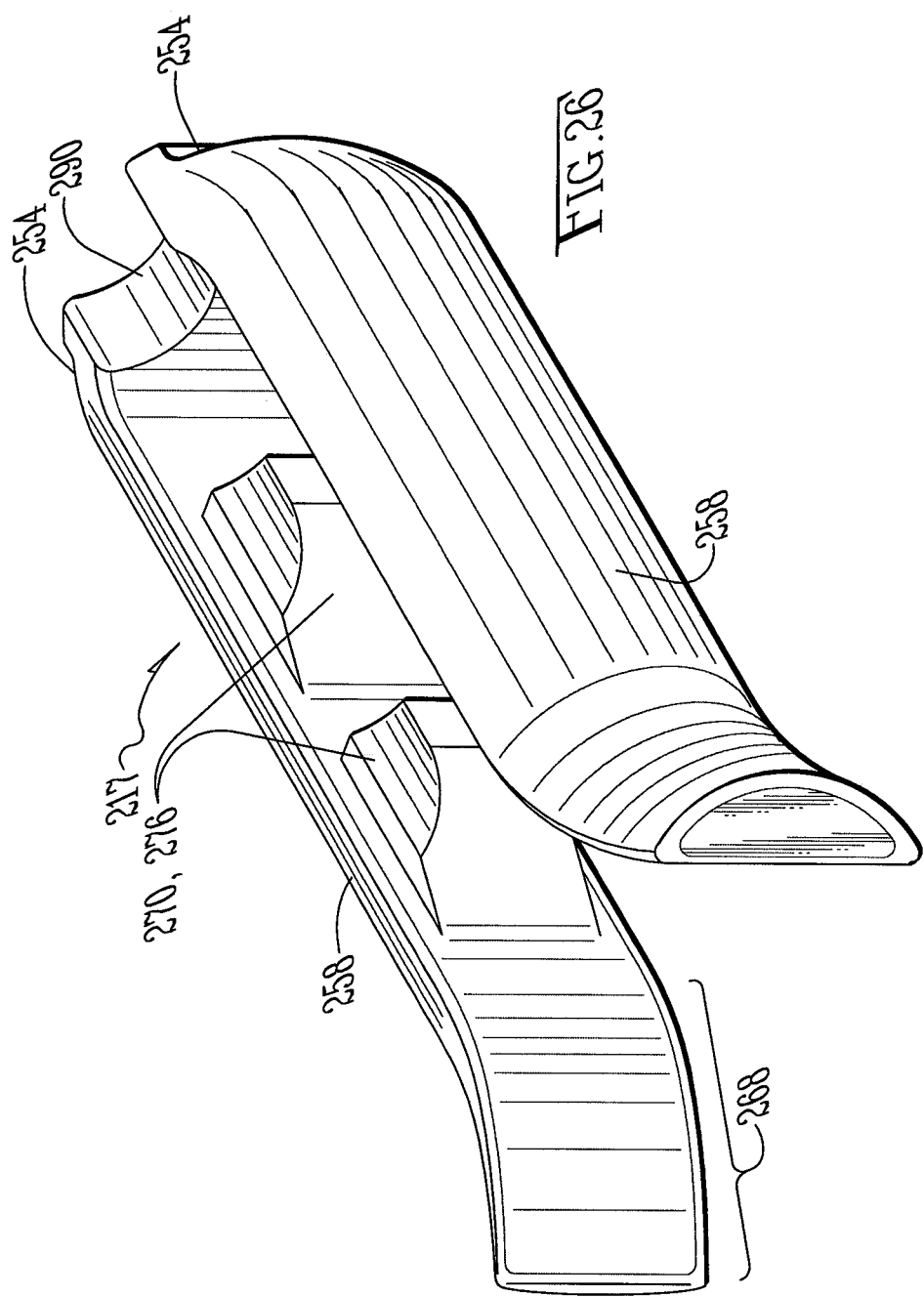
FIG. 26 is a perspective view comparable to FIGS. 9, 13, 17 and 22 except of a seventh embodiment of a surgery clip in accordance with the invention.
Figure 27:
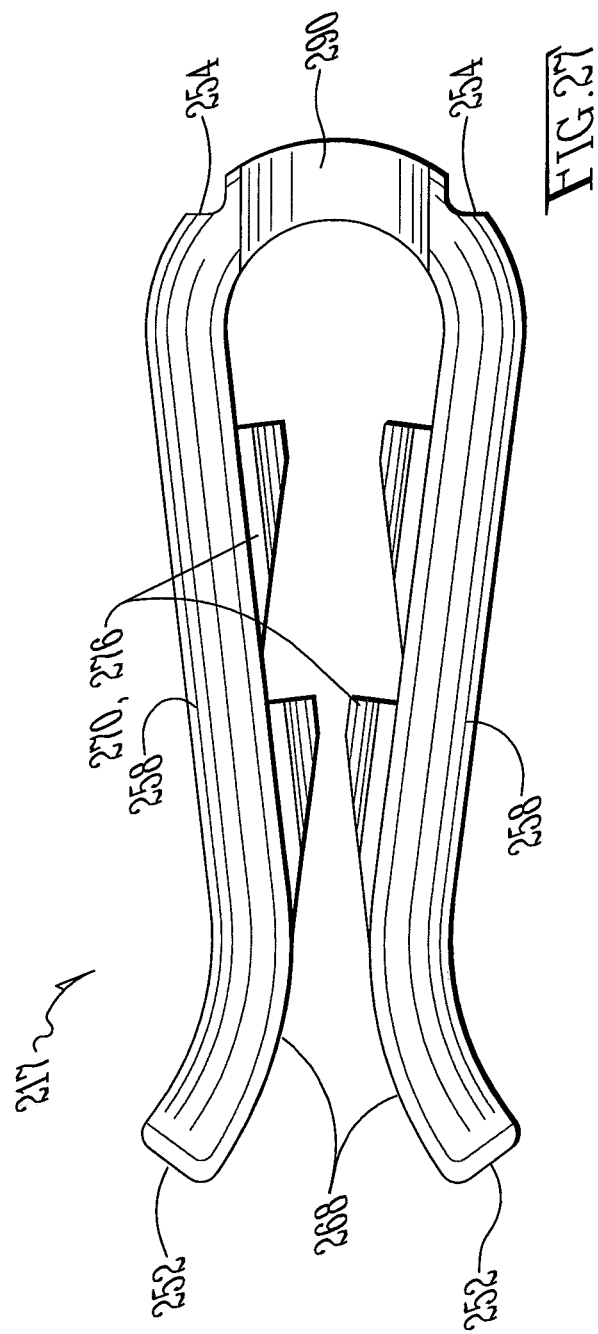
FIG. 27 is a top plan view of FIG. 26.

FIG. 25 shows how a counterpart spring 292 to the U-shaped springs shown previously and which is embedded in the tail 294 of this clip 216 in FIG. 25, simulates the bite of a clothespin. However, In FIG. 25, this counterpart spring 292 is not a simple U-shape. Indeed, the U-shape is defined the extensions which extend into the jaws 258 of the clip 216 only. That is, the U-shape is oriented laying on one side. If the U-shape of the spring 292 were oriented such that the bight opened downwardly, this would more naturally resemble an Ω-shape (ie., the capital Greek letter Omega). However, this Ω-shaped portion of the spring 292 has two lever provisions 296 emanating from spaced positions on the crown of the Ω-shape. Overall, this 'dual-levered Ω-shaped' spring 292 operates in much the same way as a clothespin. When the lever provisions 296 are pinched, the lower extensions of the Ω-shape (eg., jaw extensions 298) open up. When the lever provisions 296 are released, the lower extensions 298 of the Ω-shape (eg., jaw extensions) close due to the inherent resiliency of the crown of the Ω-shape.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. An elongated endoscopic apparatus for clipping then severing peduncular-style polyps characterized by stems extending out from an anatomical wall and terminating in bulb ends, comprising:
   an elongated flexible catheter having a generally cylindrical sidewall and extending between a dispensing end and a control end;
   said catheter being formed with at least one conduit that defines a generally cylindrical hollow core that terminates in an opening through the dispensing end, said opening being spaced in an eccentric relationship with the dispensing end such that a smallest gap between the opening and the sidewall at the dispensing end defines a perigee gap along an apogee-perigee axis that intersects the centers of both the opening and the dispensing end;
   an endoscopic clip loaded into the core proximate the opening in the dispensing end of the catheter, said clip comprising a C-shape characterized by a pair of elongated jaws mated together at a tail end, said clip being oriented in the core such that the jaws are opposed to one another flanking the apogee-perigee axis and the tail end trails behind the jaws when dispensed out the opening;
   a clip applier for dispensing the clip out the opening; and
   a snare provision disposed inside the core concurrently with the clip and controllable to reciprocate axially between extension and retraction strokes, wherein said clip is further oriented to be disposed between the snare provision and the perigee gap;
   whereby clipping procedures are performed with portions of the sidewall of the catheter encompassing the perigee gap lie on or close to the anatomical wall such that the jaws are oriented to flank the stem and urge the snare provision to a plane or planes above the clip and below the bulb.

2. The endoscopic apparatus of claim 1, wherein:
   the snare provision comprises a wire loop.

3. The endoscopic apparatus of claim 2, wherein:
   during extension strokes, the loop opens suitably for looping over the bulb end of the target polyp and encircle the stem prior to dispensing the clip around the stem, and thereafter following retraction strokes, the wire loop cinches closed and ultimately severs the stem.

4. The endoscopic apparatus of claim 1, wherein:
   the jaws have tip ends; and
   further comprising a plurality of said endoscopic clips, loaded into the core in tip end to tail procession.

5. The endoscopic apparatus of claim 4, wherein:
   the clip applier comprises a plunger rod being controllable for pushing the procession of clips through the core at an incrementally indexed or metered dispensing rate of one clip at a time.

6. The elongated endoscopic apparatus of claim 4, wherein:
   the snare provision comprises a wire loop; and
   further comprising a flexible sleeve in which the wire loop is threaded through.

7. The endoscopic apparatus of claim 6, wherein:
   said sleeve being controllable to reciprocate axially in the core between extension and retraction strokes independently of the wire loop.

8. The endoscopic apparatus of claim 6, wherein:
   each clip further comprises a notch in the tail end wherein the notches of the procession of clips cooperatively define an axially extending groove or mini-lumen within the core for the snare provision to occupy and extend and retract therein, and not interfere with clip dispensing.

9. The endoscopic apparatus of claim 1, further comprising:
   a source of illumination; and
   a camera;
   wherein the source of illumination and camera are disposed at the dispensing end of said catheter and flanking the apogee-perigee axis, with opening for the at least one conduit eccentrically situated among the source of illumination, the camera and the perigee gap.

10. An elongated endoscopic apparatus for clipping then severing peduncular-style polyps characterized by stems extending out from an anatomical wall and terminating in bulb ends, comprising:
    an elongated flexible catheter having a generally cylindrical sidewall and extending between a dispensing end and a control end;
    said catheter being formed with at least one conduit that defines a generally cylindrical hollow core that terminates in an opening through the dispensing end;
    an endoscopic clip loaded into the core proximate the opening in the dispensing end of the catheter, said clip comprising a C-shape characterized by a pair of elongated jaws mated together at a tail end;
    a clip applier for dispensing the clip out the opening; and
    a snare provision disposed inside the core concurrently with the clip and controllable to reciprocate axially between extension and retraction strokes;
    whereby clipping procedures are performed in a sequence with the snare provision undergoing an extension stroke, the clip is dispensed oriented with the jaws flanking the stem and disposed between the snare provision and the anatomical wall thereby providing an urging force to the snare provision to a plane or planes above the clip and below the bulb.

11. The endoscopic apparatus of claim 10, wherein:
    the snare provision comprises a wire loop.

12. The endoscopic apparatus of claim 11, wherein:
    during extension strokes, the loop opens suitably for looping over the bulb end of the target polyp and encircle the stem prior to dispensing the clip around the stem, and thereafter following retraction strokes, the wire loop cinches closed and ultimately severs the stem.

13. The endoscopic apparatus of claim 10, wherein:
    the jaws have tip ends; and
    further comprising a plurality of said endoscopic clips, loaded into the core in tip end to tail procession.

14. The endoscopic apparatus of claim 13, wherein:
    the clip applier comprises a plunger rod being controllable for pushing the procession of clips through the core at an incrementally indexed or metered dispensing rate of one clip at a time.

15. The elongated endoscopic apparatus of claim 13, wherein:
    the snare provision comprises a wire loop; and
    further comprising a flexible sleeve in which the wire loop is threaded through.

16. The endoscopic apparatus of claim 15, wherein:
    said sleeve being controllable to reciprocate axially in the core between extension and retraction strokes independently of the wire loop.

17. The endoscopic apparatus of claim 15, wherein:
each clip further comprises a notch in the tail end wherein the notches of the procession of clips cooperatively define an axially extending groove or mini-lumen within the core for the snare provision to occupy and extend and retract therein, and not interfere with clip dispensing.

18. The endoscopic apparatus of claim 10, further comprising:
a source of illumination; and
a camera;
wherein the source of illumination, the camera and opening are all disposed eccentrically about the dispensing end and in a triangular disposition among one another.

* * * * *